United States Patent
Norman et al.

US007494774B2

(10) Patent No.: US 7,494,774 B2
(45) Date of Patent: Feb. 24, 2009

(54) **ASSAY AND COMPOSITIONS FOR DETECTION OF *BACILLUS ANTHRACIS* NUCLEIC ACID**

(75) Inventors: Sylvia Ann Norman, Poway, CA (US); Jennifer Jill Bungo, San Diego, CA (US); James J. Hogan, Coronado, CA (US); William G. Weisburg, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 374 days.

(21) Appl. No.: 10/712,654

(22) Filed: Nov. 12, 2003

(65) Prior Publication Data

US 2008/0176221 A1 Jul. 24, 2008

Related U.S. Application Data

(60) Provisional application No. 60/426,552, filed on Nov. 15, 2002, provisional application No. 60/471,082, filed on May 16, 2003.

(51) Int. Cl.
*C12Q 1/68* (2006.01)
*C12P 21/04* (2006.01)
*C12P 21/06* (2006.01)
*C07H 21/04* (2006.01)
*A61K 39/07* (2006.01)

(52) U.S. Cl. .................... 435/6; 435/69.1; 435/69.7; 435/91.2; 536/23.1; 536/23.7; 536/24.31; 536/24.32; 536/24.33; 424/246.1

(58) Field of Classification Search .................... 435/6, 435/91.2, 69.1, 69.7; 536/23.1, 24.32, 24.33, 536/23.7, 24.31; 424/246.1
See application file for complete search history.

(56) References Cited

U.S. PATENT DOCUMENTS

| | | | |
|---|---|---|---|
| 5,591,631 A | 1/1997 | Leppla et al. | |
| 5,614,361 A | 3/1997 | Webster, Jr. | |
| 5,677,274 A | 10/1997 | Leppla et al. | |
| 5,840,312 A | 11/1998 | Mock et al. | |
| 5,874,046 A | 2/1999 | Megerle | |
| 6,087,104 A | 7/2000 | Yamada et al. | |
| 6,156,501 A | 12/2000 | McGall et al. | |
| 6,448,016 B1 | 9/2002 | Rastogi et al. | |
| 6,485,925 B1 | 11/2002 | Duesbery et al. | |
| 6,811,984 B1 | 11/2004 | Rastogi et al. | |
| 6,846,633 B1 | 1/2005 | Rastogi et al. | |
| 2002/0042051 A1 | 4/2002 | Wittwer | |
| 2002/0051791 A1 | 5/2002 | Galloway et al. | |
| 2002/0055628 A1 | 5/2002 | Keim et al. | |
| 2003/0170263 A1 | 9/2003 | Williamson et al. | |
| 2003/0232402 A1 | 12/2003 | Stender et al. | |

FOREIGN PATENT DOCUMENTS

| | | | |
|---|---|---|---|
| EP | 03815297 A4 | 8/2007 | |
| JP | 06253846 A | 9/1994 | |
| JP | 06253847 A | 9/1994 | |
| JP | 06261759 A | 9/1994 | |
| JP | 06261760 A | 9/1994 | |
| JP | 11004692 A | 1/1999 | |
| JP | 11004693 A | 1/1999 | |
| WO | WO 00/58505 A1 | 10/2000 | |
| WO | 0121656 A | 3/2001 | |
| WO | WO 01/49823 A2 | 7/2001 | |
| WO | WO02/04646 | 1/2002 | |

OTHER PUBLICATIONS

Sequence alignments of SEQ.ID.No. 21, 22, 23 and 24 with the SEQ.ID.No. 4 of Lee et al.*
Roche Media Release, "New Rapid Anthrax Test developed through collaboration between Roche Diagnostics and Mayo Clinic", Nov. 5, 2001, F. Hoffmann-LaRoche Ltd., Basel, CH.
Friedlander, "Anthrax", Textbook of Military Medicine: Medical Aspects of Chemical and Biological Warfare, 1997, Ch. 22:467-478, Borden Inst., Walter Reed Army Med. Ctr.,US.
LeBlanc et al., "Less than One Hour Detection of *Bacillus anthracis* Spores and Vegetative Cells . . . ", (undated),p. 1-4, Infectio Diagnostic Inc., Quebec, CA.
Little et al., "Comparative Efficacy of *Bacillus anthracis* Live Spore Vaccine and Protective Antigen Vaccine . . . ", Infection & Immunity, May 1986;52(2):509-512, ASM, US.
Sacchi, et al., "Sequencing of 16S rRNA Gene: A Rapid Tool for Identification of *Bacillus anthracis*", Emerging Infectious Diseases, Oct. 2002;8(10):1117-23, CDC, US.
Center for Disease Control and Prevention, "Summary of the Laboratory Response Network", Apr. 17, 2002:1-2, CDC, US.
Center for Disease Control and Prevention, "Laboratory Response Network (LRN)", Mar. 24, 2003: 1-18, CDC, US.
Roche Diagnostics GmbH, Roche Applied Science, Package Insert for "LightCycler—*Bacillus anthracis* Detection Kit," Instruction Manual, Version 1, Nov. 2001, Cat. No. 3 303 411 (23 pg).
Dickey et al., "A Non-Amplified DNA Probe Test for the Idetification of *Bacillus anthracis* from Culture," Poster #157, ASM Meeting, "Future Directions for Biodefense Research: Development of Countermeasures," held in Baltimore, MD, Mar. 9-12, 2003, ASM, Washington, D.C., USA.
Vaillancourt et al., "Development of a multiplex PCR assay for the specific detection of *Bacillus anthracis* Using the Smart Cycler" 101st General Meeting of the ASM, held in Orlando,FL, May 2001 (reprinted with permission by Cepheid, at www.cepheld.com).

(Continued)

*Primary Examiner*—Shanon A. Foley
*Assistant Examiner*—Padma V Baskar
(74) *Attorney, Agent, or Firm*—Christine A. Gritzmacher

(57) ABSTRACT

The invention includes compositions and methods of detection of *Bacillus anthracis* that use oligonucleotide probes specific for genetic material contained in the pXO1 and pXO2 plasmids in nucleic acid hybridization reactions. Embodiments of the method may include additional probes specific for other gene sequences to distinguish *B. anthracis* from other bacterial species present in a sample or to provide an indication that the assay was performed properly even when no *Bacillus* sequence is detected.

12 Claims, No Drawings

OTHER PUBLICATIONS

Makino S-I et al., "Molecular Characterization and Protein Analysis of the Cap Region, which is essential for encapsulation in *Bacillus anthracis*," J. Bacteriology, Feb. 1989, pp. 722-730, vol. 171, No. 2, American Society for Microbiology, Washington, D.C., US.

Reif T. C. et al., "Identification of Capsule-Forming *Bacillus anthracis* Spores with the PCR and a Novel-Dual Probe Hybridization Format" Appl. & Environ. Microbiology, May 1994, pp. 1622-1625, vol. 60, No. 5, American Society for Microbiology, Washington, D.C. US.

Ramisse V. et al., "Identification and Charaterization of *Bacillus anthracis* by multiplex PCR Analysis of Sequences on Plasmids pXO1 and PXO2 and Chromosomal DNA" FEMS Microbiology Letters, Nov. 15, 1996, pp. 9-16, vol. 145, No. 1, Elsevier, Amsterdam, NL.

Castro A. et al., "Ultrasensitive, Direct Detection of a Specific DNA Sequence of *Bacillus anthracis* in Solution" Analyst, 2000, pp. 9-11, vol. 125, No. 1, Royal Soc. of Chemistry, London, GB.

Iqbal S. S. et al., "A Review of Molecular Recognition Technologies for Detection of Biological Threat Agents" Biosensors & Bioelectronics, Dec. 2000, pp. 549-578, vol. 15, No. 11-12, Elsevier Science Publishers, Barking GB.

Bell C. A. et al., "Direct Detection of *Bacillus anthracis* Using a Real-Time PCR Method" Abstracts of Gen. Mtg. Amer. Soc. Microbiol. May 2001, p. 155, vol. 101, No. 155, American Society for Microbiology, Washington, D.C., US Makino S-I et al., "Detection of Anthrax Spores from the Air by Real-Time PCR" Ltrs in Appl. Microbiol., Sep. 2001, pp. 237-240, vol. 33, No. 3, The Society for Applied Microbiology, Oxford, GB.

Bell C. A. et al., "Detection of *Bacillus anthracis* DNA by Lightcycler PCR" Journal of Clinical Microbiol. Aug. 2002, p. 2897-2902, vol. 40, No. 8, American Society for Microbiology, Washington, D.C., US.

* cited by examiner

ASSAY AND COMPOSITIONS FOR DETECTION OF *BACILLUS ANTHRACIS* NUCLEIC ACID

RELATED APPLICATIONS

This application claims the benefit under 35 U.S.C. 119(e) of provisional application No. 60/471,082, filed May 16, 2003, and provisional application No. 60/426,552, filed Nov. 15, 2002, both of which are incorporated by reference herein.

FIELD OF THE INVENTION

This invention relates to detection of *Bacillus anthracis*, the causative agent of anthrax, and more specifically to compositions and methods for detecting plasmid-borne nucleic acid sequences that distinguish *B. anthracis* from other *Bacillus* species.

BACKGROUND OF THE INVENTION

*Bacillus anthracis* is a spore-forming bacterium that is the causative agent of anthrax, a disease that often attacks lungs or connective tissue. Cutaneous anthrax is the most common form of the disease which causes skin redness, boils or ulceration after *B. anthracis* spores infect injured skin or membranes and germinate to vegetative cells that produce anthrax toxin. If bacteremia develops, it may lead to high fever and death. The respiratory form occurs following inhalation of spores which infect alveolar macrophages and germinate in lymph nodes causing edema, hemorrhaging, lymph node necrosis and pleural effusion. Respiratory anthrax, which is usually fatal within a week of infection, may lead to septicemia and meningitis. Oropharyngeal and gastrointestinal anthrax are the least common forms of the disease, which usually result from ingestion of contaminated meat that has been insufficiently cooked. Although uncommon and beginning with nonspecific symptoms (sore throat, fever, nausea, vomiting), these forms of anthrax have about a 50% mortality rate. Although anthrax usually attacks herbivorous animals, humans who come in contact with contaminated animal hair, wool, hides, meat, or waste can contract the disease. Human infection caused by deliberate release of *B. anthracis* spores, resulting in cutaneous and/or respiratory anthrax, is a form of biological warfare or bioterrorism. Infected humans can be treated for anthrax by using antibiotics, e.g., penicillin. Accurate detection of the presence of *B. anthracis* and diagnosis of infection is important because of the high fatality rate of the disease and the risk to others who may be exposed to an infected individual or contaminated items.

*B. anthracis* is related to other species in the *Bacillus* genus, all of which are endospore forming bacteria that are gram-positive rods. *B. anthracis* is closely related to commonly occurring non-anthrax species, such as *B. cereus, B. cereus* var *mycoides, B. thuringiensis, B. megaterium* and *B. subtilis*. Because of the close genetic relationships of *B. cereus, B. cereus* var *mycoides, B. anthracis*, and *B. thuringiensis*, these species are often grouped as members of the *B. cereus* complex, or even considered one species (Kaneko et al., 1978, *Microbiol Immunol.* 22: 639-41; Helgason et al., 2000, *Appl. Environ. Microbiol.* 66: 2627-30). For example, this relationship is exhibited in the gene sequences encoding 16S rRNA (1,554 nt), in which there are one to four nt differences between the genes of *B. anthracis, B. cereus*, and *B. thuringiensis* strains, although the *B. anthracis* sequence was highly conserved for 86 strains tested and the *B. thuringiensis* sequence was highly conserved for 11 strains tested (Sacchi et al., 2002, *Emerging Infect. Dis.* 8(10): 1117-23).

Virulent strains of *B. anthracis* carry virulence genes on two plasmids, pXO1 and pXO2 (GenBank accession nos. AF065404 and AF188935, respectively). Genes on plasmid pXO1 code for proteins that contribute to the toxicity of *B. anthracis* infection: protective antigen (PA), edema factor (EF), and lethal factor (LF). PA is a membrane-binding protein required for toxicity when combined with either EF or LF. The gene pag codes for PA, the gene cya codes for EF, and the gene lef codes for LF (Price et al., 1999, *J. Bacteriol.* 181(8):2358-2362). Genes on plasmid pXO2, designated capB, capC, and capA, code for elements of the antiphagocytic capsule of *B. anthracis*. Known strains of *B. anthracis* retain both, one or none of these plasmids. Generally, a strain that has lost one or both of these plasmids is considered avirulent. A virulent strain contains both plasmids, such as the Ames (pXO1+/pXO2+) strain. An avirulent strain that has lost the pXO2 plasmid is strain Δ Sterne (pXO1+/pXO2−), spores of which are used worldwide as a live vaccine for animals (Hambletone et al., 1984, *Vaccine* 2: 125-32). An avirulent strain that has lost the pXO1 plasmid is strain Δ Ames (pXO1−/pXO2+). Strains that have lost both plasmids are known, e.g., strain VNR1-Δ1.

Clinical identification of *B. anthracis* relies on procedures such as microscopic examination of Gram-stained smears made from a specimen or cultured bacteria, detection of non-hemolytic or weakly hemolytic growth on blood agar, observation of granular or ground-glass texture of colonies grown for greater than 36 hrs on agar media, or mucoid colonies which are associated with virulent encapsulated forms (Logan et al., In: *Manual of Clinical Microbiology*, 7th Ed., Murray et al., eds., 1999, American Society for Microbiology (Washington, D.C.), pp. 357-69). Under microscopic examination, *B. anthracis* cells are large rods, usually in chains and encapsulated, which generally are nonmotile compared to motile strains of *B. cereus* and *B. thuringiensis*. *B. anthracis* rods may or may not contain oval central or subterminal spores, which form when the bacteria are exposed to low $CO_2$ levels such as found in the atmosphere. Clinical testing for *B. anthracis* includes preparing and examining laboratory cultures made from the sample, e.g., inoculating broth and blood cultures and streaking on laboratory media such as 5% sheep blood agar, MacConkey agar, and phenyl ethyl alcohol agar. Cultures are incubated for at least 3 days and observed daily beginning as early as 8 hours after inoculation to determine the growth characteristics of the bacteria or colonies. While hemolysis, gram stain morphology, or motility results can be used to rule out the presence of *B. anthracis*, a combination of two test results is recommended to rule out *B. anthracis* as the organism present in the tested sample. Because other members of the *B. cereus* complex group may mimic *B. anthracis* in appearance and characteristics, interpreting test results is challenging and definitive identification of *B. anthracis* from culture is difficult. Additional assays for identification of *B. anthracis* have relied on detecting encapsulated organisms by using antibodies, and detecting α-glucosidase activity. These tests usually require at least 3 days to rule out the presence of *B. anthracis* or for positive identification of the *Bacillus* species because of the relatively long growth period of colonies in the laboratory. Moreover, clinical laboratories that perform these tests require equipment to permit procedures be done at a biosafety level of 2 (BSL-2) or greater. If a clinical laboratory is unable to rule out the presence of *B. anthracis* or definitively identify the *Bacillus* species, then the sample is referred to another laboratory for further testing.

In addition to these clinical tests, other methods may be used to detect and identify *Bacillus* species, including *B. anthracis* (Harrell et al., 1995, *J. Clin. Microbiol.* 33: 1847-1850; Keim et al., 1999, *J. Appl. Microbiol.* 87(2): 215-7; Jackson et al., 1997, *Appl. Environ. Microbiol.* 63(4): 1400-5; Sirard et al., 2000, *Int. J. Med. Microbiol.*, 290(4-5): 313-6); Mock et al., 2001, *Ann. Rev. Microbiol.* 55: 647-71). For example, *B. anthracis* has been detected by using tests based on the polymerase chain reaction (PCR) to amplify bacterial nucleic acid sequences that identify *B. anthracis* (Makino et al., 1993, *J. Clin. Microbiol.* 31(3): 547-51; Ramisse et al., 1996, *FEMS Microbiol. Lett.* 145(1): 9-16; Makino et al., 2001, *Lett. App. Microbiol.* 33(3): 237-40; Keim et al., 1997, *J. Bacteriol.* 179(3): 818-24; Patra et al., 1998, *J. Clin. Microbiol.* 36(11): 3412-14; Daffonchio et al., 1999, *Appl. Environ. Microbiol.* 65(3): 1298-303; Lee et al., 1999, *J. Appl. Microbiol.* 87(2): 218-23; Fasanella et al., 2001, *Vaccine* 19(30): 4214-18; Enserink, 2001, *Science* 294(5545): 1266-7). Another method of detecting *B. anthracis* relies on detecting *B. anthracis*-specific polymorphic signature sequences isolated from chromosomal DNA (Rastogi et al., U.S. Pat. No. 6,448,016 B1). One assay relies on amplifying and detecting species-specific fragments of the gyrB genes to distinguish between *B. cereus*, *B. thuringiensis*, and *B. anthracis* (Yamada et al., U.S. Pat. No. 6,087,104).

Because of the clinical significance of anthrax infections, and the additional psychological and economic impacts of bioterrorism threats or events that may involve *B. anthracis*, there remains a need for effective methods to detect and identify *B. anthracis* that may be present in environmental and clinical samples (Lane and Fauci, 2001, *JAMA* 286:2596-7; Enserink, 2001, *Science* 294(5545): 1266-7). There is a particular need to identify and distinguish virulent forms of *B. anthracis* from non-virulent *B. anthracis* or other similar *Bacillus* species. Initial testing of samples in the United States may be done at a Level A clinical laboratory (of the Laboratory Response Network for Bioterrorism ("LRN"), categorized by the Centers for Disease Control and Prevention ("CDC"), Atlanta, Ga., USA) that is not be equipped or trained to identify *Bacillus* species, and then samples suspected of containing *B. anthrax* are referred to other laboratories (e.g., LRN Level B or C) for further testing. To avoid delays in identification of the *Bacillus* species or unnecessary referrals to higher level laboratories for identification, there remains a need for an assay that quickly allows a Level A laboratory to at least rule out the presence of *B. anthracis* from a tested sample and more preferably to identify the presence of *B. anthracis* in a sample.

SUMMARY OF THE INVENTION

One aspect of the invention is an oligonucleotide of about 20 to about 40 nucleotides that hybridizes specifically to a sequence contained in a *B. anthracis* target sequence of SEQ ID NO:21, SEQ ID NO:22, SEQ ID NO:23, SEQ ID NO:24, SEQ ID NO:25, SEQ ID NO:26, SEQ ID NO:34, a complementary sequence, or RNA equivalent of any one of the target sequences. Embodiments of such oligonucleotides include an oligonucleotide that hybridizes specifically to a pagA target sequence contained in the sequence of SEQ ID NO:21, SEQ ID NO:22, SEQ ID NO:23, or SEQ ID NO:24, a complementary sequence, or RNA equivalent of any one of the pagA target sequences. Examples of oligonucleotides that hybridize specifically to these pagA target sequences include oligonucleotides of SEQ ID NO:1 or SEQ ID NO:2 that hybridize specifically to SEQ ID NO:21, oligonucleotides of SEQ ID NO:3 or SEQ ID NO:4 that hybridize specifically to SEQ ID NO:22, oligonucleotides of SEQ ID NO:5 or SEQ ID NO:6 that hybridize specifically to SEQ ID NO:23, and oligonucleotides of SEQ ID NO:7 or SEQ ID NO:8 that hybridize specifically to SEQ ID NO:24. Other embodiments of the invention include oligonucleotides that hybridize specifically to a capB target sequence contained in the sequence of SEQ ID NO:25 or SEQ ID NO:26, a complementary sequence, or RNA equivalent of any one of the capB target sequences. Examples of oligonucleotides that hybridizes specifically to SEQ ID NO:25 are oligonucleotides of SEQ ID NO:9, SEQ ID NO:10, SEQ ID NO:11, or SEQ ID NO:12. Examples of oligonucleotides that hybridizes specifically to SEQ ID NO:26 are oligonucleotides of SEQ ID NO:13 or SEQ ID NO:14. An additional embodiment of the invention is an oligonucleotide of about 18 to 40 bases that hybridizes specifically to a 16S rRNA or DNA encoding a 16S rRNA sequence of a *Bacillus* species contained in a target sequence of SEQ ID NO:31, a complementary sequence, or RNA equivalent thereof. Examples of such oligonucleotides include those of SEQ ID NO:15, SEQ ID NO:16, SEQ ID NO:17, SEQ ID NO:18, SEQ ID NO:19, SEQ ID NO:20, SEQ ID NO:37, SEQ ID NO:38, or SEQ ID NO:39. Another embodiment of the invention is an oligonucleotide of about 20 to 50 bases that hybridizes specifically to a 23S rRNA or DNA encoding a 23S rRNA sequence of a *Bacillus* species contained in a target sequence of SEQ ID NO:32, a complementary sequence, or RNA equivalent thereof. Examples of such oligonucleotides include those of SEQ ID NO:27, SEQ ID NO:28, SEQ ID NO:29, SEQ ID NO:30, SEQ ID NO:35, or SEQ ID NO:36. Any of these oligonucleotides may have a DNA or RNA backbone, or mixed DNA and RNA backbone, or contain at least one 2'-methoxy RNA group linking the bases. Any of these oligonucleotides may include a signal-producing label linked directly or indirectly to the oligonucleotide. A preferred label is a chemiluminescent compound.

Another aspect of the invention is a method of detecting *B. anthracis* nucleic acid in a sample that includes the steps of providing a sample containing *B. anthracis* nucleic acids, providing at least one probe that hybridizes specifically to a pagA target sequence contained in a pXO1 plasmid and at least one probe that hybridizes specifically to a capB target sequence contained in a pXO2 plasmid, hybridizing specifically at least one probe to the pagA target sequence, or at least one probe to the capB target sequence, or at least one probe to the pagA target sequence and at least one probe to the capB target sequence, and detecting the presence of at least one probe hybridized to the pagA target sequence or to the capB target sequence to indicate the presence of *B. anthracis* in the sample. In an embodiment of the method, the pagA target sequence is contained in the sequence of SEQ ID NO:33, or a complementary sequence, or RNA equivalent thereof, and the capB target sequence is contained in the sequence of SEQ ID NO:34, or a complementary sequence, or RNA equivalent thereof. In some embodiments of the method, the pagA target sequence is contained in a sequence of SEQ ID NO:21, SEQ ID NO:22, SEQ ID NO:23, or SEQ ID NO:24, a complementary sequence, or RNA equivalent of any one of these sequences, and the capB target sequence is contained in a sequence of SEQ ID NO:25 or SEQ ID NO:26, a complementary sequence, or RNA equivalent or any one of these sequences. In some embodiments, the hybridizing step includes at least one probe specific for the pagA target sequence which is an oligonucleotide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or at least one probe specific for a capB target sequence which is an oligonucleotide of SEQ ID NO:9, SEQ ID NO:10, SEQ ID NO:11, SEQ ID NO:12, SEQ ID NO:13, or SEQ ID NO:14. Some embodiments of the method further include the steps of providing at least one probe that hybridizes specifically to a 16S or 23S rRNA sequence or DNA encoding a 16S or 23S rRNA sequence conserved among species of the *B. cereus* complex, hybridizing at least one probe to the 16S or 23S rRNA sequence or DNA encoding the 16S or 23S rRNA sequence conserved among species of the *B. cereus* complex, and detecting the presence of at least one probe hybridized to the 16S or 23S rRNA sequence or DNA encoding the 16S or 23S rRNA sequence conserved among species of the *B. cereus* complex, thereby indicating the presence of a *B. cereus* complex organism in the sample. In a preferred embodiment, at least one probe that hybridizes specifically to a 16S rRNA or DNA encoding a 16S rRNA sequence is an oligonucleotide of 18 to 40 bases that hybridizes specifically to a sequence contained in SEQ ID NO:31, a complementary sequence, or RNA equivalent thereof. Such oligonucleotides include those having a sequence of SEQ ID NO:15, SEQ ID NO:16, SEQ ID NO:17, SEQ ID NO:18, SEQ ID NO:19, SEQ ID NO:20, SEQ ID NO:37, SEQ ID NO:38, or SEQ ID NO:39. Another embodiment of the method uses at least one probe that hybridizes specifically to a 23S rRNA or DNA encoding a 23S rRNA sequence which is an oligonucleotide of 20 to 50 bases that hybridizes specifically to a sequence contained in the sequence of SEQ ID NO:32, a complementary sequence, or RNA equivalent thereof. Such oligonucleotides include those of SEQ ID NO:27, SEQ ID NO:28, SEQ ID NO:29, SEQ ID NO:30, SEQ ID NO:35, or SEQ ID NO:36. In another embodiment of the method, the providing step includes a probe that hybridizes specifically to a genetic sequence present in eubacterial species, the hybridizing step includes hybridizing the probe specifically to the genetic sequence present in eubacterial species, and the detecting step includes detecting the probe hybridized to the genetic sequence present in eubacterial species, thereby indicating that the method steps have been performed properly when no *Bacillus* sequences are detected in the assay. In a preferred embodiment, the probe has a sequence of SEQ ID NO:40, and detecting this probe hybridized to a rRNA or DNA encoding rRNA in the assay indicates the presence of a eubacterium in the sample. Additional embodiments of the invention include a kit for practicing the method, which includes at least one probe that hybridizes to a sequence contained in the pagA target sequence of SEQ ID NO:21, SEQ ID NO:22, SEQ ID NO:23, or SEQ ID NO:24, a complementary sequence, or RNA equivalent of any one of these sequences, and at least one probe that hybridizes specifically to a sequence contained in the capB target sequence of SEQ ID NO:25 or SEQ ID NO:26, a complementary sequence, or RNA equivalent or any one of these sequences. A kit may include at least one probe specific for the pagA target sequence which is an oligonucleotide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, and at least one probe specific for a capB target sequence which is an oligonucleotide of SEQ ID NO:9, SEQ ID NO:10, SEQ ID NO:11, SEQ ID NO:12, SEQ ID NO:13, or SEQ ID NO:14.

The following detailed description illustrates various embodiments of the invention which serve to explain the principles of the invention.

DETAILED DESCRIPTION

The invention provides a method for detecting *B. anthracis* nucleic acid in a sample by providing a sample containing *B. anthracis* nucleic acids, hybridizing at least two detection probes that bind specifically and independently to genetic sequences contained in pXO1 and pXO2 plasmids of *B. anthracis*, and detecting the presence of a probe bound to pXO1 genetic material and/or a probe bound to pXO2 genetic material to indicate the presence of *B. anthracis* in the sample. The method may include growing organisms in a biological sample in vitro and lysing the organisms in the sample to release *B. anthracis* nucleic acids. The method may also include a step of binding at least one labeled probe to a rRNA sequence specific to *Bacillus* 16S or 23S rRNA, in which the sequence bound by the probe is conserved among species of the *B. cereus* complex (i.e., *B. anthracis*, *B. thuringiensis*, and *B. cereus*) and detecting the presence of a the probe bound to rRNA or DNA encoding an rRNA sequence to indicate the presence of a *B. cereus* complex organism in the sample. For example, the method may include a step of binding at least one labeled probe specific to *Bacillus* 16S rRNA sequence that is completely conserved between *B. anthracis*, *B. thuringiensis* and *B. cereus*, but is less than completely conserved between *B. anthracis* and *B. mycoides*, i.e., the bound sequence contains at least one nucleotide difference between *B. anthracis* and *B. mycoides*. Detecting the presence of the probe bound to the 16S rRNA sequence indicates the presence of a *B. anthracis* or another species of the *B. cereus* complex in the sample. Also, for example, the method may use at least one detection probe, and optionally one or more helper oligomers with the detection probe, to hybridize to and detect the presence of a 23S rRNA sequence to indicate the presence of *B. anthracis* and/or a closely related *Bacillus* species. Another embodiment of the method includes hybridizing a probe that binds specifically to a eubacterial rRNA or DNA encoding rRNA sequence to produce a signal that indicates that the assay steps were performed appropriately, even if *Bacillus* or *B. anthracis* sequence were not detected with another probe in the assay. Such a step served as an internal control for the assay.

The invention includes nucleic acid sequences of oligonucleotides that bind specifically to *B. anthracis* genetic sequences contained in plasmids pXO1 and pXO2, namely to the target sequences contained within the sequences of SEQ ID NO:21, SEQ ID NO:22, SEQ ID NO:23, SEQ ID NO:24, SEQ ID NO:25, or SEQ ID NO:26. Oligonucleotides that bind to the target sequences may be in a length range of 20 to 40 nucleotides, preferably in the range of 25 to 35 nucleotides. Embodiments of such oligonucleotides include those having the sequence of SEQ ID NO:1 through SEQ ID NO:14. Other oligonucleotides useful for practicing the methods of the invention include those specific for a 16S rRNA sequence of *Bacillus* species that hybridize specifically to the target sequence of SEQ ID NO:31, which include oligonucleotides of SEQ ID NO:15 through SEQ ID NO:20, and those specific for a 23S rRNA sequence of *Bacillus* species that hybridize specifically to the target sequence of SEQ ID NO:32, which include oligomers of SEQ ID NO:27 through SEQ ID NO:30. Additional embodiments of oligonucleotides that hybridize specifically to DNA sequences that encode *Bacillus* rRNA are exemplified by SEQ ID NO:36 and SEQ ID NO:37. Oligonucleotides of the invention include those that have a DNA or RNA backbone, or mixed DNA and RNA sequences, or contain at least one 2'-methoxy RNA group linking the bases. These oligonucleotides may include a signal-producing label which is directly or indirectly linked to the oligonucleotide.

The invention includes oligonucleotides that contain nucleic acid sequences that hybridize specifically to selected sequences of the pXO1 and pXO2 plasmids of *B. anthracis*. The invention includes methods of detecting the presence of

*B. anthracis* in a sample by detection of nucleic acid probes that hybridize specifically to sequences of the pXO1 and pXO2 plasmids. Embodiments specifically detect sequences contained in the pagA gene of plasmid pXO1 (GenBank accession no. M22589) and the capB gene of plasmid pXO2 (in GenBank accession no. AF188935). Some embodiments are oligomers that bind specifically to sequences of the pXO1 plasmid contained in the sequences of SEQ ID NO:21 through SEQ ID NO:24, whereas other embodiments are oligomers that bind specifically to sequences of the pXO2 plasmid contained in the sequences of SEQ ID NO:25 and SEQ ID NO:26.

To aid in the understanding the description of the invention, definitions of some of the terms used herein are provided. Unless defined otherwise, all scientific and technical terms used herein have the same meaning as commonly understood by those skilled in the relevant art, such as provided in the *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and *Dorland's Illustrated Medical Dictionary*, 27th ed. (W. A. Dorland, 1988, W.B. Saunders Co., Philadelphia, Pa.).

"Complementary" nucleic acids (or "complementarity") refers to a nucleic acid sequence in one strand of nucleic acid, which due to orientation of functional groups, will hybridize, generally via hydrogen bonds, to another nucleic acid sequence on an opposing strand. Standard base pairing in DNA means that an adenine (A) in one strand bonds to thymine (T) in an opposing strand, and cytosine (C) bonds to guanine (G) on an opposing strand. In RNA, the same bonding relationship occurs except that uracil (U) replaces T and bonds to A in an opposing strand. "Substantial complementarity" or "substantially complementary" means that a nucleic acid sequence in one strand is less than 100% complementary to a nucleic acid sequence in an opposing strand, but that sufficient hydrogen bonds form between complementary bases to allow the two strands to form a stable complex in appropriate conditions (e.g., salt solution concentration and temperature). "Sufficient complementarity" or "sufficiently complementary" means a contiguous nucleic acid sequence hybridizes to another contiguous nucleic acid sequence by hydrogen bonding between complementary bases under the hybridization conditions used. Complementary sequences may be complementary at each position in the sequence by using standard base pairing (e.g., G:C, A:T or A:U pairing), or may contain one or more residues that are not complementary using standard hydrogen bonding (such as by bonding to inosine or another analog, including a basic residues), but the entire complementary sequence is capable of specifically hybridizing with another sequence in appropriate hybridization conditions. Appropriate hybridization conditions are well known, and can be predicted readily based on sequence composition or determined empirically by using routine testing (e.g., see Sambrook et al., *Molecular Cloning, A Laboratory Manual* (2nd Ed.), Vol. 1-3, 1989 (Cold Spring Harbor Laboratory, Cold Spring Harbor, N.Y.), pp. 1.90-1.91, 7.37-7.57, 9.50-9.51, 11.12-11.13, and 11.47-11.57). Nucleic acid oligomers may contain additional moieties (e.g., a label attached directly to the nucleic acid or indirectly via a linker moiety) without destroying complementarity.

"Hybridization condition" refers to the cumulative environment used for a reaction in which one single-stranded nucleic acid binds to a complementary or substantially complementary sequence in a second single-stranded nucleic acid to produce a stable hybridization complex (or simply "complex"). Such an environment includes, for example, compounds and concentrations of components of an aqueous or organic solution (e.g., salts, chelating agents, noncompetitive inhibitor nucleic acid, pH) containing the single-stranded nucleic acids, the reaction temperature, and may be influenced by other factors, e.g., the amount of time in which hybridization is allowed to occur, the geometry of the reaction chamber, and the use of mixing or agitation (e.g., see Sambrook et al., at pp. 1.90-1.91, 9.47-9.51, 11.47-11.57).

A "label" refers to a molecular moiety that can be detected or can lead to a detectable signal, for example, by participating in a reaction that produces a detectable product. A label may be, for example, a luminescent (such as fluorescent, bioluminescent, or chemiluminescent) moiety, a radioisotope, biotin, avidin, enzyme or enzyme substrate, reactive group, or a chromophore (such as a dye or particle that imparts a detectable color).

A "labeled probe" is a nucleic acid sequence, preferably a DNA or RNA oligomer, associated directly or indirectly with a detectable moiety, e.g., a fluorescent or luminescent moiety, radioisotope, biotin, avidin, enzyme or catalytic group, enzyme substrate, chromophore or reactive group. Examples of production and/or use of such labeled probes are well known (Sambrook et al., Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333; and Becker et al., European Patent App. Pub. No. 0 747 706).

A "helper oligomer" or "helper probe" refers to a nucleic acid oligomer that binds to the target nucleic acid in a region different than that bound by the labeled probe, which is used to increase the efficiency of hybridization of a labeled probe oligomer to its target sequence (Hogan et al., U.S. Pat. No. 5,030,557). Helper oligomers generally are designed to bind to sequences in the target nucleic acid that contain predicted secondary or tertiary structure and are situated close to the target sequence of the probe oligomer with the aim of accelerating the rate of binding of the oligonucleotide probe to its target sequence. Although helper oligonucleotides are not labeled when used in conjunction with labeled probes, they facilitate binding of labeled probes and so indirectly enhance detectable signals resulting from hybridization. Although one or more helper oligomers may be included in a hybridization reaction to increase efficiency of binding of the labeled probe to its target sequence, helper oligomers are optional components of the assay.

"Nucleic acid" refers to a polydeoxyribonucleotide (DNA or analog thereof) or polyribonucleotide (RNA or analog thereof) of at least two, and preferably 10 or more nucleotides (nt) in length. The term "nucleic acid" includes polynucleotides, oligonucleotides or oligomers, and polymeric DNA and RNA molecules, whether single-stranded (ss), double-stranded (ds), or triple-stranded. It will be understood that the nucleic acid sequences disclosed herein may be either DNA or RNA, and a base sequence encompasses its corresponding sequence with the alternative backbone (i.e., RNA or DNA), or a backbone that includes 2'-methoxy groups or other nucleic acid analogs, e.g., peptide linkages.

"Oligonucleotides" or "oligomers" refer to nucleic acid sequences composed of at least two nucleotides, joined via a backbone of phosphodiester linkages (in DNA or RNA), modified linkages, or non-nucleotide moieties that do not prevent hybridization of the oligonucleotide to its complementary target sequence. Modified linkages include those in which a standard phosphodiester linkage is replaced with a different linkage, such as a phosphorothioate, methylphosphonate, or polyamide linkage (e.g., in peptide nucleic acids or "PNA"). Nitrogenous base analogs may be components of oligonucleotides and the sugar groups of the nucleotide subunits may be ribose, deoxyribose, or modified derivatives thereof such as OMe. Oligomers generally have eight or more linked nucleotides, usually up to about 100 nucleotides in length. Methods of synthesizing oligonucleotides and analog sequences are well known in the art (e.g., see *Oligonucleotide Synthesis: A Practical Approach*, Gait, ed. (IRL Press, Oxford, 1984), Kuijpers, *Nucl. Acid Res.* 18(17): 5197 (1994), Ducholm, *J. Org. Chem.* 59: 5767 (1994), U.S. Pat. No. 5,143,854 (Pirrung et al.), and U.S. Pat. No. 6,156,501 (McGall et al.)). Oligomer probes may optionally have a detectable label conjugated, directly or indirectly, to the nucleic acid. Routine protocols are available to allow a skilled person to incorporate a label into a nucleic acid probe. For use in hybridization, probes generally are rendered single-stranded to allow efficient complementary base pairing with its target sequence (e.g., Sambrook et al., pp. 11.1-11.61).

A "target" or "target sequence" refers to a nucleic acid sequence to which a probe sequence binds by using complementary base pairing. A target sequence for one or more probe sequences may be a subset of a larger target sequence, e.g., a complete gene sequence. For example, "probe A" has a complementary "target sequence A" and "probe B" has a complementary "target sequence B", and a larger "target sequence C" that comprises both "target sequence A" and "target sequence B" may comprise additional target sequences. In another example, "probe A" and "probe B" have sequences complementary to different subsets of a "gene X target sequence." In another example, multiple probes have different but overlapping sequences and those multiple probes bind to a target sequence that is complementary to the cumulative contiguous sequence of the multiple overlapping probe sequences.

"$T_m$" refers to the melting temperature at which a population of hybridization complexes formed between two nucleic acid strands are 50% denatured. At a temperature below the $T_m$ for the two nucleic acid strands, formation of a stable hybridization complex is favored, whereas at a temperature above the $T_m$, complex formation is disfavored. $T_m$ can be determined empirically by using routine methods or estimated by using known mathematical formulae. For example, a simple estimate of $T_m$ for a nucleic acid having a known G+C content in an aqueous 1M NaCl solution is calculated by using the equation $T_m=81.5+0.41(\% \text{ G+C})$, although other computations that take into account structural characteristics of the nucleic acid are also well known in the art (e.g., $T_m=0.401(\text{nt length})+0.576(\% \text{ G+C})+24.852$).

Selection of oligonucleotide probes for detecting an intended target sequence by specific hybridization relies on a number of considerations, including the length and nucleotide base composition of the probe, and the thermal stability ($T_m$) of the probe-target hybridization complex (see Sambrook et al., at pp. 11.45-11.57). Longer probes generally have greater stability, but shorter probes often have greater specificity because of increased mismatch discrimination, i.e., the occurrence of a base mismatch between a short probe and its target has a greater destabilizing effect on the duplex than the mismatch would have if a longer probe were used. Generally, probe oligomers are in a size range of about 18 to 50 nucleotides, preferably in a range of 25 to 35 nucleotides. In addition to the $T_m$ of a probe-target duplex, the internal structure of a probe oligomer or its target may also influence hybridization efficiency. For example, self-complementary sequences can form higher order structures, such as intramolecular hairpin turns or intermolecular multihybrid complexes, that may interfere with hybridization between a probe and its target. Therefore, potentially self-complementary sequences are avoided in selecting probe and target sequences. Probes or targets may be attached, directly or indirectly, to a solid support such as a filter, membrane, bead, slide or chip, although solution phase hybridization provides for more efficient kinetics compared to solid phase hybridization.

By "consisting essentially of" is meant that additional component(s), composition(s), or method step(s) that do not materially change the basic and novel characteristics of the present invention may be included. Such characteristics include the detection of *B. anthracis* strains carrying both plasmids pXO1 and pXO2 by using at least two nucleic acid probes that hybridize specifically to genetic sequences on the plasmids pXO1 and pXO2, e.g., at least one probe specific for pagA sequences of plasmid pXO1 and at least one probe specific for capB sequences of plasmid pXO2. Relative to the disclosed oligonucleotide probes that specifically bind to and detect the pagA gene of plasmid pXO1 and the capB gene of plasmid pXO2, changes are not considered material if the changes to a specific probe sequence, which might increase or decrease the probe sequence length, permit the changed probe sequence to hybridize to the intended target sequence of the specific probe sequence and to distinguish virulent from non-virulent *B. anthracis* strains using the conditions described herein. Relative to the disclosed methods for detecting *B. anthracis* strains by using at least two nucleic acid probes that hybridize specifically to the pagA gene of plasmid pXO1 and the capB gene of plasmid pXO2, changes are not considered material if the changes to the method, which may include adding or substituting reagents (e.g., nucleic acids or other components) or adding steps to the assay, if they do not interfere with specific hybridization of the at least two probes with their respective target sequences or detection of the probes bound to their respective target sequences under conditions disclosed herein. Any component(s), composition(s), or method step(s) that has a material effect on the basic and novel characteristics of the present invention would fall outside of this term.

Unless mentioned otherwise, the techniques employed or contemplated herein are standard methodologies well known to a person of ordinary skill in the art (e.g., see Sambrook et al., *Molecular Cloning, A Laboratory Manual* (2nd Ed.), Vol. 1-3, 1989 (Cold Spring Harbor Laboratory, Cold Spring Harbor, N.Y.)).

Nucleic Acid Sequences for Detecting *B. anthracis* Genetic Sequences

The invention includes nucleic acid sequences of oligonucleotides that bind specifically to *B. anthracis* genetic material contained in plasmids pXO1 and pXO2, and optionally in 16S and/or 23S rRNA or genes encoding rRNA. Generally, the oligonucleotides were designed to select for sequences that display a minimum of self-annealing secondary structure, with a $T_m$ in the range of 59° C. to 75° C., a length range of 20 to 50 nucleotides, and a G+C percentage in the range of 40 to 64%.

The target sequences in plasmids pXO1 and pXO2 are contained within the pagA sequence of pXO1 and the capB sequence of pXO2. More specifically, target sequences are contained in the pagA sequences of SEQ ID NO:21, SEQ ID NO:22, SEQ ID NO:23, SEQ ID NO:24, and the capB sequences of SEQ ID NO:25 and SEQ ID NO:26. Embodiments of oligonucleotides that bind to these target sequences may be in the range of about 20 to 40 nucleotides in length, preferably in the range of about 25 to 35 nucleotides. Embodiments of such oligonucleotides include those having the sequences of SEQ ID NO:1 through SEQ ID NO:8 for pagA target sequences, and SEQ ID NO:9 through SEQ ID NO:14 for capB target sequences. Embodiments of the oligonucleotides include those that have a DNA or RNA backbone, mixed DNA and RNA sequences, or at least one 2'-methoxy RNA linkage group. Some embodiments of the oligonucleotides include a signal-producing label which may be directly or indirectly linked to the oligonucleotide.

In addition to nucleic acid sequences and methods for detecting gene sequences of the pXO1 and pXO2 plasmids of *B. anthracis*, probes for detecting sequences of the 16S or 23S rRNA or genes encoding rRNA of *Bacillus* species of the *B. cereus* complex are useful in these methods for detecting an organism of the *B. cereus* complex group which may be distinguished from other bacilli or non-Bacillus organisms. When the detection of genetic material of the pXO1 and/or pXO2 plasmids is combined with detection of 16S or 23S rRNA or genes encoding rRNA of the *B. cereus* complex group, the combined information is useful for distinguishing virulent *B. anthracis* from avirulent strains or other species of the *B. cereus* complex. For example, if a sample provides a positive detection signal for rRNA sequences or genes encoding rRNA of the *B. cereus* complex, but negative signals for both of the pXO1 and pXO2 target sequences, then one may reasonably conclude that the sample does not contain pathogenic *B. anthracis* but contains another species of the *B. cereus* complex or a non-pathogenic *B. anthracis* strain (i.e., one that lacks both plasmids, pXO1−/pXO2−). If a sample provides a positive detection signal for rRNA sequences or genes encoding rRNA of the *B. cereus* complex, and a positive signal for one of the pXO1 and pXO2 plasmid target sequences, then one may reasonably conclude that the sample contains *B. anthracis* that is missing one plasmid (pXO1−/pXO2+ or pXO1+/pXO2−, depending on which positive signal is detected). Similarly, if a sample provides a positive detection signal for rRNA sequences or genes encoding rRNA of the *B. cereus* complex, and a positive signal for both of the pXO1 and pXO2 plasmid target sequences, then one may reasonably conclude that the sample contains a *B. anthracis* strain that contains both plasmids (pXO1+/pXO2+), as in a wild-type *B. anthracis* strain. In most cases, the information useful for detecting the presence of *B. anthracis* in a sample would be detection of a positive signal from probes for one or both plasmids (i.e., pXO1−/pXO2+ or pXO1+/pXO2− or pXO1+/pXO2+ strains), and a positive result for detection of 16S or 23S rRNA or genes encoding rRNA of the *B. cereus* complex would provide confirmatory information on the presence of *B. anthracis* in the sample.

For designing oligonucleotides specific for rRNA or genes encoding rRNA of *B. anthracis*, genes encoding both 16S and 23S rRNA and the known genetic sequences encoding rRNA from a variety of *Bacillus* species, including *B. anthracis*, were compared and oligonucleotides were selected that are complementary to regions where the *B. anthracis* sequences exhibit significant divergence from sequences in the same regions of closely related *Bacillus* species, except for those of *B. thuringiensis* and *B. cereus*. For example, for selection of oligonucleotide probe sequences for the 23S rRNA sequence of *B. anthracis*, the known 23S rRNA sequence of *B. anthracis* (Genbank accession no. AF267734) was compared to aligned known 23S rRNA sequences of *B. thuringiensis, B. cereus, B. mycoides, B. megaterium, B. licheniformis, B. stearothermophilus*, and *B. globisporus*. Regions that exhibited the highest amount of divergence between *B. anthracis* (and *B. thuringiensis* and *B. cereus*) compared to the other species were selected as potential targets. Then, specific probe oligomers were designed using the criteria described above (e.g., limited predicted secondary structure, appropriate GC content and $T_m$). Similar steps were performed for designing probes specific for *B. anthracis* 16S rRNA or genes encoding rRNA by comparing the *B. anthracis* sequence (Genbank accession no. AF176321) to aligned known sequences of *B. thuringiensis, B. cereus, B. mycoides, B. megaterium, B. licheniformis, B. globisporus*, and *B. stearothermophilus*. Oligomers that may serve as helper oligonucleotides were designed and targeted to regions situated close to the target sequences for the designed probes, particularly directed to regions that contain predicted higher order structure (as described previously by Hogan et al., U.S. Pat. No. 5,030,557). As used in the examples that follow, a helper oligonucleotide refers to an oligonucleotide that was designed to enhance the kinetics of hybridization between the labeled probe and its target sequence and/or to increase the extent of hybridization between the labeled probe and its target sequence, even though such designed helper oligomers may not have performed optimally under the particular conditions described for the embodiments illustrated by the examples.

Oligonucleotides useful for detection of 16S rRNA sequences of *Bacillus* species include those that hybridize specifically to the target sequence of SEQ ID NO:31 or its complementary strand sequence or RNA equivalent. Embodiments of such oligonucleotides include those of SEQ ID NO:15 through SEQ ID NO:20 and their complementary or DNA or RNA sequences. In some embodiments, combinations of two or more of these oligonucleotides facilitate detection of the 16S rRNA target sequences where one or more of the oligomers is a labeled probe and one or more oligonucleotides is unlabeled and acts as a helper oligonucleotide to increase the efficiency of hybridization of the labeled probe with its target sequence. Embodiments of helper oligomers include those of SEQ ID NO:17 and SEQ ID NO:18 or their complementary or RNA sequences.

Oligonucleotides useful for detection of 23S rRNA sequence of *Bacillus* species include those that hybridize specifically to the target sequence of SEQ ID NO:32 or its complementary strand sequence or RNA equivalent. Embodiments include oligomers of SEQ ID NO:27 through SEQ ID NO:30, SEQ ID NO:35 and SEQ ID NO:36 and their complementary or RNA sequences. In some embodiments, combinations of two or more of these oligonucleotides facilitate detection of the 23S rRNA target sequences where one or more of the oligomers is an unlabeled helper oligomer. Embodiments of such helper oligomers include those of SEQ ID NO:27 and SEQ ID NO:29 or their complementary or RNA sequences. Additional oligomers may be included in the assay to independently confirm that appropriate hybridization conditions were achieved. Such additional oligomers include those that hybridize to eubacterial sequences as previously described (Hogan et al., U.S. Pat. No. 5,679,520). Embodiments of eubacterial probe and helper oligomers are those of SEQ ID NOS 40 to 43.

Methods for Detecting *B. anthracis* Nucleic Acids

For use in the detection methods of the invention, a sample is provided that may contain *B. anthracis* organisms (which includes viable spores, living bacteria, or mixtures thereof). The sample may be from any source including biological specimens or environmental samples and may contain other biological (viable or inviable) or inert materials in addition to *B. anthracis* organisms. For example, a biological sample or biological specimen includes any tissue derived from a living or dead organism which may contain a *B. anthracis* organism. Such samples include, for example, hemorrhagic fluids, peripheral blood, bone marrow, plasma, biopsy tissue including from cutaneous lesions, lymph nodes, oropharyngeal tissue, respiratory tissue or exudates or lavage, gastrointestinal tissue, nervous system tissue (e.g., brain tissue, meninges, cerebral spinal fluid), urine, feces, semen, or other body fluids or tissues of human or animal origin. Care should be taken in handling samples that may contain *B. anthracis* to avoid contamination of surfaces and/or personnel with live cells or spores. Generally, the sample is innoculated into or on an appropriate microbial medium and incubated to allow *Bacillus* organisms to grow using well known microbiological techniques (e.g., streaked onto a blood agar plate and grown for 18 to 24 hr). The culture may be used to provide phenotypic information about the organisms present in the sample (e.g., colony morphology, hemolytic activity). The cultured sample is then used to make a lysate of organisms to release nucleic acids for testing for the presence of *B. anthracis* nucleic acids, particularly sequences carried on the pXO1 and pXO2 plasmids.

Typically, biological material is taken from the cultured sample (e.g., one or more colonies from an agar plate or about 2 to 4 µl of liquid culture) and lysed to release nucleic acids using any of a variety of well-known methods (e.g., see Sambrook et al. at pp. 1.22-1.39, Graves L. M. et al., "Universal Bacterial DNA Isolation Procedure", in *Diagnostic Molecular Microbiology, Principles and Applications*, (Persing et al., eds.), 1993, American Society for Microbiology (Washington, D.C.), pp. 617-622, Murphy et al., U.S. Pat. No. 5,374,522, and Kacian et al., U.S. Pat. No. 5,386,024). Because the cultured sample may contain infectious organisms, the sample is preferably treated to kill viable organisms and inactivate spores and to cause lysis. One method involves mixing about two to four loopfuls of bacteria (about 2 to 4 µl) taken from an agar plate with a lysis buffer containing detergent (e.g., about 0.35 to 0.7 ml of 0.1% lithium lauryl sulfate (LLS), 20 mM lithium succinate, pH 5.5, 1 mM EDTA), heating the mixture to 90 to 105° C. for 15 min, and sonicating the mixture for 15 min (e.g., in a water bath sonicator). The lysate may be cooled (e.g., on ice) to help maintain the single-stranded DNA form (ssDNA) of the target sequences. Following lysis, cellular debris may be separated from the liquid by gravitation or centrifugation using standard methods (e.g., in a microcentrifuge for 1 min). Additional sample preparation steps may be included, such as, for example, hydrolysis of RNA in the lysate (e.g., for use with a probe specific for detecting a DNA target). Hydrolysis of RNA can be accomplished by adding a base solution to the lysate (e.g., a final concentration of 0.8M LiOH, heating the mixture (e.g., 60° C. for 15 min), and then neutralizing the base (e.g., with an acid and buffer).

An aliquot of the lysate is used in a hybridization reaction with at least two nucleic acid oligomer probes, at least one specific for a gene normally carried on the pXO1 plasmid and at least one specific for a gene normally carried on the pXO2 plasmid. The probe oligomers hybridize to nucleic acid sequences in the lysate by complementary base pairing under conditions that form a stable hybridization complex in which the probe is specifically bound to its complementary target sequence. Such hybridization conditions are well known in the art and can be readily determined for nucleic acid probes of any sequence and length by performing routine testing (e.g., Sambrook et al. at pp. 1.90-1.91, 9.47-9.53, and 11.55-11.57). Formation of a stable hybridization complex between an probe and its intended target may result from hybridization in which all of the bases of the probe are completely complementary to the target sequence or in which the bases in the probe are substantially complementary to the intended target sequence. Detection probes of the present invention are at least 80% complementary to their intended target and more preferably are in a range of between 90 to 100% complementary to their target sequence. The target sequence to which an oligomer probe binds may be in any form that allows formation of a stable hybridization complex. For example, the target nucleic acid may be complete and intact, such as in a complete gene or gene cloned into a plasmid (supercoiled or relaxed circles, or linearized forms), or the target nucleic acid may be a fragment, such as a contiguous sequence that contains a portion of the target gene, so long as the target sequence is sufficient to allow the probe to bind and form a stable hybridization complex.

Hybridization conditions and methods are well known and have been described in detail elsewhere (e.g., Sambrook et al. at pages 1.101-1.102, 9.47-9.62, 11.7-11.8, 11.12-11.13, 11.17-11.19, 11.45-11.61, Appendices B, C, and E). Solution phase hybridization is preferred because of the favored kinetics associated with it (Kohne, U.S. Pat. No. 4,851,330). For example, an aliquot of a bacterial lysate, such as described above, is mixed with a hybridization buffer, such as a buffered salt solution, and with at least the nucleic acid probes that hybridize independently and specifically to sequences on the pXO1 and pXO2 plasmids. Additional probes or nucleic acids can be included in the mixture, such as a probe to hybridize to a known sequence that serves as an internal control or calibrator for the assay. The mixture is incubated for minutes to hours at a temperature below the $T_m$ of the probes for their respective target sequences to allow hybridization of the probes to their targets. The $T_m$ of a probe may be calculated by using a standard logarithm based on the oligomer length and GC content (e.g., $T_m=0.401$(nt length)+0.576(% G+C)+24.852) or the $T_m$ of a probe may be determined empirically by using standard methods (Sambrook et al. at 11.55-57). Following hybridization, the stable complexes are detected by using any of a variety of known methods, e.g., detecting a signal associated with the probe, or resulting from the probe binding to the target, or resulting from the probe interacting with another substance that yields a signal, such as an enzyme or enzyme substrate. In one embodiment, for example, 50 µl to 100 µl of the lysate is mixed with an equal volume of a hybridization buffer (e.g., 0.9M phosphate buffer, pH 5, 0.16% SDS), and the labeled nucleic acid probes (0.2 pmol of each) for pagA and capB target sequences. The mixture is incubated below the calculated $T_m$ of the oligomer probes and their respective targets (e.g., at 55 to 60° C. for 20 min to 1 hr) to allow the probe and target sequences to hybridize specifically. Stable hybridization complexes are detected by using any suitable method that detects the probes present in stable hybridization complexes.

Detection of probe-target stable hybridization complexes may be accomplished after removing unbound oligomers and detecting the remaining probes (i.e., those bound in the complexes), whether they are detected in the complexes or subsequently separated from the complexes. Detection of stable hybridization complexes may be accomplished by using a homogeneous system in which bound probes are distinguished from unbound probes. In preferred embodiments, a homogeneous detection step is used to detect, in a mixture, a labeled probe that is bound to its respective target nucleic acid (e.g., Arnold et al., *Clin. Chem.* 35:1588-1594 (1989), Nelson et al., U.S. Pat. No. 5,658,737, and Lizardi et al., U.S. Pat. Nos. 5,118,801 and 5,312,728, the details of which are incorporated by reference). A "homogeneous detectable label" may be directly or indirectly attached to a probe oligomer and the label is detected based on whether the probe hybridized to the target polynucleotide. Because the bound homogeneous detectable label is distinguishable from label on unbound probes, it can be detected without physically separating hybridized from unhybridized labeled probes. Such homogeneous detectable labels are known, as are methods of attaching them to nucleic acid oligomers and detecting them (Arnold et al., U.S. Pat. No. 5,283,174, Woodhead et al., U.S. Pat. No. 5,656,207, and Nelson et al., U.S. Pat. No. 5,658,737). For the methods of the present invention, any detection apparatus capable of detecting a signal from the label may be used. In the embodiments illustrated below, chemiluminescent signals ("relative light units" or RLU) were detected in homogeneous detection reactions by using a luminometer (e.g., GEN-PROBE® LEADER®, Gen-Probe Incorporated, San Diego, Calif.).

A preferred label for use in a homogenous assay is a chemiluminescent compound (e.g., U.S. Pat. Nos. 5,656,207, 5,658,737 and 5,639,604). Such chemiluminescent labels include acridinium ester ("AE") compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE. A preferred label is a chemiluminescent AE compound attached to the probe sequence via a linker substantially as described previously (Arnold et al., U.S. Pat. No. 5,585,481; Arnold et al., U.S. Pat. No. 5,639,604, particularly column 10, line 6 to column 11, line 3, and Example 8, the technical details of which are incorporated by reference). For example, for the oligonucleotide probes described herein AE labels were attached between nt 14 and 15 for SEQ ID NO:1, SEQ ID NO:8, SEQ ID NO:14, SEQ ID NO:28 and SEQ ID NO:30, between nt 12 and 13 for SEQ ID NO:3, SEQ ID NO:9, SEQ ID NO:10, SEQ ID NO:11, and SEQ ID NO:12, between nt 10 and 11 for SEQ ID NO:13, between nt 11 and 12 for SEQ ID NO:15 and SEQ ID NO:16, between nt 9 and 10 for SEQ ID NO:4, SEQ ID NO:6 and SEQ ID NO:7, between nt 13 and 14 for SEQ ID NO:5 and SEQ ID NO:7, and between nt 19 and 20 for SEQ ID NO:2. Additional embodiments of oligonucleotide probes include those in which an AE label was attached between nt 8 and 9, or nt 11 and 12 for SEQ ID NO:1; between nt 11 and 12, or nt 14 and 15, or nt 20 and 21 for SEQ ID NO:4; and between nt 15 and 16, or nt 18 and 19 for SEQ ID NO:7.

Kits for Detecting pXO1 and pXO2 Nucleic Acid Sequences

The present invention also embraces kits for performing assays to detect the presence of *B. anthracis* by using at least one nucleic acid oligomer that hybridizes specifically to a target sequence contained in the pagA gene sequence and at least one nucleic acid oligomer that hybridizes specifically to a target sequence contained in the capB genetic sequence. Embodiments of such kits contain at least one nucleic acid oligomer sufficiently complementary to a target sequence contained in any one of SEQ ID NO:21, SEQ ID NO:22, SEQ ID NO:23 or SEQ ID NO:24 to allow specific hybridization to the target sequence, and at least one nucleic acid oligomer sufficiently complementary to a target sequence contained in SEQ ID NO:25 or SEQ ID NO:26 to allow specific hybridization to the target sequence. Certain preferred kits further contain at least one nucleic acid oligomer that hybridizes specifically to a 16S or 23S rRNA sequence or genes encoding rRNA of the *B. cereus* complex group. Embodiments of such kits contain nucleic acid oligomers that are sufficiently complementary to allow specific hybridization to a target sequence specific for 16S rRNA or its coding sequence contained in SEQ ID NO:31, its complementary sequence or RNA equivalents thereof, and/or nucleic acid oligomers that are sufficiently complementary to allow specific hybridization to a target sequence for 23S rRNA or its coding sequence contained in SEQ ID NO:32, its complementary sequence, or RNA equivalents thereof. Other embodiments of kits include at least one nucleic acid probe that serves as an internal control because it hybridizes to and detects a eubacterial target sequence even if a *Bacillus* species is not present. Preferred embodiments of eubacterial probes hybridize specifically to rRNA or DNA encoding rRNA sequences.

Exemplary kits include at least one nucleic acid oligomer that binds specifically to the pagA target sequence, which oligomer consists of a sequence of any one of SEQ ID NO:1 through SEQ ID NO:8, and at least one nucleic acid oligomer that binds specifically to the capB target sequence, which oligomer consists of a sequence of any one of SEQ ID NO:9 through SEQ ID NO:14. Other embodiments of kits may also include, in addition to at least one pagA-specific oligomer and at least one capB-specific oligomer, an oligomer that binds specifically to a target sequence of rRNA or DNA sequence encoding rRNA of the *B. cereus* complex group, such as an oligomer that consists of any one of SEQ ID NO:15 through SEQ ID NO:20 and SEQ ID NO:27 through SEQ ID NO:30. Kits that include an oligomer that binds specifically to a target sequence of rRNA or DNA encoding rRNA of the *B. cereus* complex group may include at least one labeled probe oligomer and at least one unlabeled helper oligomer, both of which are specific for the respective rRNA or DNA encoding rRNA target. Embodiments of such kits include those that contain oligomers specific for the target sequence of 16S rRNA or DNA encoding rRNA, where labeled oligomers have a sequence that consists of any one of SEQ ID NO:15, SEQ ID NO:16, SEQ ID NO:19 and SEQ ID NO:20, and the unlabeled helper oligomers have a sequence that consists of any one of SEQ ID NO:17 and SEQ ID NO:18. Other embodiments of such kits include those that contain oligomers specific for the target sequence of 23S rRNA or DNA encoding rRNA, where labeled oligomers have a sequence that consists of SEQ ID NO:28 or SEQ ID NO:30, and the unlabeled helper oligomers have a sequence that consists of SEQ ID NO:27 and SEQ ID NO:29. Other embodiments include oligomers in which SEQ ID NO:40 is a labeled probe and one or more helper oligomers of SEQ ID NO:41, SEQ ID NO:42, and SEQ ID NO:43 is optionally included. It will be understood that kits of the present invention may include any combination of such nucleic acid oligomers provided that there is at least one pagA-specific oligomer and at least one capB-specific oligomer.

Kits may also contain reagents, including oligonucleotides, that may be used to partially purify the *B. anthracis* nucleic acid to be detected in hybridization reactions in vitro. For example, a kit may contain one or more oligomers that serve as capture oligomers for purifying the pXO1 and/or pXO2 target nucleic acid from a sample. Examples of capture oligomers have sequences of at least 15 nucleotides complementary to a portion of the pXO1 and/or pXO2 plasmid nucleic acid. Such capture oligomers do not need to hybridize specifically to a sequence in either the pagA or capB gene sequences because capture oligomers serve to partially purify and concentrate the plasmids that contain these gene sequences, rather than the specific genes, from a sample. Such a capture step is in addition to the hybridization reactions to detect the presence of the plasmids. Embodiments of capture oligomers have sequences complementary to a sequence in the pXO1 and/or pXO2 nucleic acid. Capture oligomers may have covalently attached 3' or 5' sequences that are not complementary to the plasmid nucleic acid but that hybridize to complementary sequences to capture the target nucleic acid as described in detail previously (Weisburg et al., U.S. Pat. No. 6,110,678).

Kits useful for practicing the methods of the present invention may include those that include any of the nucleic acid oligonucleotides disclosed herein which are packaged in combination with each other. Kits may also include capture oligomers for purifying the pXO1 and pXO2 plasmids that carry the target sequences in the pagA and capB genes from a sample, which may be packaged in combination with the probes. Thus, it will be clear to those skilled in the art, that the present invention embraces many different kit configurations.

The present invention is useful for detecting the presence of *B. anthracis* in a sample by using relatively few reagents and method steps. Because the methods do not require extensive biochemical reactions or complicated equipment, they are particularly useful for laboratories that receive samples and perform microbiology steps to grow and phenotypically examine organisms for *B. anthracis* in the samples. The relatively simple method of the invention includes the steps of hybridizing nucleic acid oligonucleotides (detection probes) to nucleic acid in a cell lysate, and detecting a label associated with hybridized oligonucleotides to indicate the presence of *B. anthracis* genetic material associated with pathogenicity in the sample. This relatively simple test lends itself to use in laboratories or field conditions where sophisticated microbiology and/or molecular biology techniques are not available or routinely practiced. Moreover, because the assay requires only a few steps with relatively short incubation periods, it detects and identifies *B. anthracis* in a sample in a relatively short period of time compared to many clinical assays. The assay relies on detection of at least two markers associated with virulence in *B. anthracis* and thus provides the advantage of detecting virulent strains compared to avirulent *B. anthracis* strains (i.e., those lacking pXO1 and/or pXO2) or other *Bacillus* species. Embodiments that also include a probe specific for detection of rRNA or genes encoding rRNA also have the advantage of narrowing the identification to possible members of the *B. cereus* complex group, which provides additional information on samples that test negative for *B. anthracis*. Embodiments that include an internal control provide additional information to indicate that the assay was properly performed even if no *Bacillus* species was detected.

The methods disclosed herein are technologically easy to perform and may be used in many laboratories including LRN Level A laboratories (network laboratories are designated by the CDC at levels A through D, with progressively stringent levels of safety, containment and technological proficiency). Because in vitro amplification procedures are not required for the assay, the potential for sample cross contamination and laboratory contamination is minimized, thus minimizing the potential of obtaining false positive results. The disclosed methods provide sensitive and specific detection of *B. anthrax* starting from about $10^7$ CFU which is equivalent to one small bacterial colony, allowing the test to be performed within 8 to 12 hours of laboratory culture of the sample, and providing test results within about one hour of beginning the assay. The disclosed methods provide a reliable and rapid assay for detection of *B. anthrax* in cultured specimens from clinical or environmental samples. Because the methods accurately identify a *Bacillus* culture in a manner that excludes non-*B. anthracis* samples (i.e., rules out samples suspected of containing *B. anthracis*), the assay rapidly identifies samples that do not require further testing, such as those containing *B. thuringiensis*. The assay also identifies samples that require further testing, such as those to be sent to a LRN level B (or higher) laboratory or to a reference laboratory for *B. anthracis* strain identification.

The general principles of the present invention may be more fully appreciated by reference to the following examples which are representative of some of the embodiments.

EXAMPLE 1

Preparation of PagA and CapB Target Sequences

Two synthetic genetic target sequences, derived from pagA and capB gene sequences, were synthesized to provide known standards for testing oligonucleotides for detection of the genes carried by the plasmids pXO1 and pXO2, without requiring handling of virulent *B. anthracis*.

The pagA target sequence (SEQ ID NO:33) consists of a subsequence of the pagA gene sequence (GenBank accession no. M22589) that was cloned from the pXO1 plasmid by using standard molecular biology techniques. Briefly, cells containing the pXO1 plasmid were grown on laboratory medium using standard microbiology methods, the cells were collected and lysed in the presence of 10 mM Tris, pH 7.5 by incubating the mixture at 95° C. for 20 min and sonicating at 60° C. for 10 to 15 min. Aliquots (0.5 to 3 µl) of the lysates were used as templates in polymerase chain reactions ("PCR", Mullis et al., U.S. Pat. No. 4,683,195) with primers to amplify a 1.108 kb fragment containing nt 2393 to 3500 of GenBank accession number M22589. The amplified synthesized fragments were purified using routine chromatographic methods and the purified fragments were sequenced to confirm that they contained SEQ ID NO:33. The purified fragments were cloned into a plasmid vector and clones containing the inserted fragment were identified. Plasmid DNA from clones were purified and the inserts were sequenced to confirm that they were SEQ ID NO:33. Purified plasmid DNA containing SEQ ID NO:33 was quantitated by using standard methods spectrophotometric methods and appropriate dilutions were made to provide known numbers of the pagA target sequence in the tests as described in some of the following examples.

The capB target sequence is a 560 bp sequence (SEQ ID NO:34) contained in the plasmid pXO2 sequence (GenBank accession no. AF188935). This capB target sequence was synthesized in vitro by hybridizing together a series of synthetic single-stranded DNA (ssDNA) oligonucleotides that contain overlapping sequences in the capB gene, i.e., each ssDNA oligomer overlapped by about 20 nt at its 5' and/or 3' ends with an end of one or two other ssDNA oligomers and the overlapping ends were hybridized at their complementary end sequences to produce a partially double-stranded DNA (dsDNA) containing the contiguous sequence. Then, complementary strands were synthesized in vitro by extending the 3' ends of the ssDNA in the partially dsDNA by using T4 DNA polymerase and using the sequence of the hybridized oligomer in the partially dsDNA as a template to form a complete dsDNA with gaps in the backbone. The ends of the synthetic strands were ligated together by using T4 DNA ligase to produce a covalently joined complete dsDNA which was amplified in a PCR reaction. The amplified DNA was purified by using routine chromatographic methods and the purified DNA fragment was cloned into a plasmid vector and transformed into an *E. coli* host cell by using standard methods. Clones containing plasmids with the expected size of the capB target fragment were identified by using routine chromatographic methods and the inserted fragments from two such clones were sequenced to show that they contained SEQ ID NO:34 (which corresponds to nt 471 to 1030 of GenBank accession no. M24150). Cloned plasmid DNA containing the capB target sequence was purified and quantitated using standard methods to provide known numbers of the capB target sequence in tests described in some of the following examples.

EXAMPLE 2

Probes for Plasmid pXO1 and Plasmid pXO2

Probes were designed by selecting regions within the pagA (SEQ ID NO:33) and capB (SEQ ID NO:34) sequences that provide a minimum of secondary structure and a $T_m$ in the range of about 59 to 75° C. This example shows the results obtained with two probes for each of the target sequences.

AE-labeled probes (0.2 pmol of each per reaction) of SEQ ID NO:4 and SEQ ID NO:7, specific for the pagA genetic sequences of plasmid pXO1, and SEQ ID NO:9 and SEQ ID NO:11, specific for the capB genetic sequences of plasmid pXO2, were used in hybridization and detection reactions to show that the probes hybridize specifically to their respective targets. The reaction mixtures were lysates of *Bacillus* (non-anthrax species) made substantially as described above using the heat and sonication method. The lysate mixture was mixed with a defined amount of the target sequence (described in Example 1) so that each individual reaction mixture contained $10^9$ or $10^{10}$ copies of the pagA genetic sequence (complementary to both SEQ ID NO:4 and SEQ ID NO:7), or $10^9$ or $10^{10}$ copies of the capB genetic sequence (complementary to both SEQ ID NO:9 and SEQ ID NO:11). The reaction mixtures were hybridized in solution at 60° C. for 20 to 30 min with 0.2 pmol of each probe per reaction in separate hybridization reactions containing probes of SEQ ID NO:4 with SEQ ID NO:7 for pagA detection, and SEQ ID NO:9 with SEQ ID NO:11 for capB detection. Following hybridization, the labels on unbound probes were hydrolyzed substantially as described previously (Arnold et al., U.S. Pat. No. 5,639,604), and the luminescence from the bound probes was detected in a luminometer as relative light units ("RLU"). A second set of experiments was performed using the same targets and probes, but also including unlabeled oligonucleotides to act as helper oligomers (2 pmol of each per reaction) as follows: unlabeled oligomers of SEQ ID NO:3 and SEQ ID NO:8 were added to hybridization reactions containing labeled probes of SEQ ID NO:4 and SEQ ID NO:7 (0.2 pmol of each), and unlabeled oligomers of SEQ ID NO:10 and SEQ ID NO:12 were added to hybridization reactions containing labeled probes of SEQ ID NO:9 and SEQ ID NO:11 (0.2 pmol of each). (The unlabeled oligonucleotides had previously been AE-labeled via linker arms, but the AE had been hydrolyzed before the oligonucleotides were added to these reactions.) Four reactions were performed for each of the combinations, and the average (mean) detected RLU for these reactions are shown in Table 1.

TABLE 1

PagA and CapB Hybridization Results

| Target Gene | Labeled Probes | Unlabeled Oligomers | Detected RLU for Target: $10^9$ Copies | Detected RLU for Target: $10^{10}$ Copies |
|---|---|---|---|---|
| pagA | SEQ ID NOs:4 & 7 | None | 18,965 | 112,916 |
| | SEQ ID NOs:4 & 7 | SEQ ID NOs:3 & 8 | 18,375 | 127,674 |

TABLE 1-continued

PagA and CapB Hybridization Results

| Target Gene | Labeled Probes | Unlabeled Oligomers | Detected RLU for Target: $10^9$ Copies | Detected RLU for Target: $10^{10}$ Copies |
|---|---|---|---|---|
| capB | SEQ ID NOs:9 & 11 | None | 29,731 | 192,718 |
| | SEQ ID NOs:9 & 11 | SEQ ID NOs:10 & 12 | 30,920 | 210,066 |

The results show detection of sequences specific for the plasmids pXO1 and pXO2 of *B. anthracis* by using the disclosed labeled oligonucleotides in hybridization reactions. The presence of unlabeled oligomers in the reactions that contained $10^{10}$ target provided somewhat greater signal for those samples compared to the similar reactions without such unlabeled oligomers.

EXAMPLE 3

Testing of Bacterial Lysates

Using the probe mixtures substantially as described in Example 2, lysates of bacterial cells prepared from overnight colonies were similarly assayed. For these tests, blood agar plates were innoculated with the bacteria which were grown overnight (18 to 24 hr). Colonies were selected from the innoculated plates and two 1-µl loopfuls of bacteria were added to 0.3 ml of lysing reagent (0.1% LLS, 20 mM lithium succinate, 1 mM EDTA, pH 5.5) and the mixture was heated at 100 to 105° C. for 15 min and then sonicated for 15 min in a water bath sonicator. For the hybridization reactions, 50 µl of the sonicated lysate was added to 50 µl of 2× hybridization reagent (20 mM EGTA, 20 mM EDTA, 2% LLS, 100 mM succinic acid, 1.2 M lithium chloride, 230 mM lithium hydroxide, pH 4.7) containing AE-labeled probes of SEQ ID NO:4 (labeled using a linker between bases 9 and 10), SEQ ID NO:7 (labeled using a linker between bases 13 and 14), SEQ ID NO:9 (labeled using a linker between bases 12 and 13) and SEQ ID NO:11 (labeled using a linker between bases 12 and 13), to achieve a theoretical maximum of $4\times10^6$ RLU per probe, and the mixture was incubated at 60° C. for 20 to 30 min to allow hybridization. The labels on the unbound probes were inactivated by hydrolysis (60° C. for 10 min after adding a base reagent at pH 8.5) and RLU detected for bound probes were measured by using a luminometer. Assays were scored as "positive" if greater than 40,000 RLU were detected, scored as "negative" if less than 20,000 RLU were detected, and scored as "equivocal" if RLU between 20,001 and 39,999 were detected. In most cases, equivocal assays were resolved to be either negative or positive by repeating the tests on one or more additional aliquots of the original lysate. The tests were performed in a "blinded" fashion, i.e., samples were prepared by one person and assays were performed by a second person who did not know what the samples contained and who learned the contents of the sample after the results were obtained. Duplicate or more assays were performed for each sample lysate. The negative control was a lysate of *B. cereus*, one positive control was a lysate of *B. anthracis* containing both pXO1 and pXO2 (pXO1+/pXO2+, Pasteur strain), and another positive control was a lysate of *B. anthrasis* containing only pXO1 plasmid (pXO1+/pXO2—, Sterne strain). *B. cereus* lysates always provided negative results, *B. anthracis* pXO1+/pXO2+ lysates always provided positive results, and *B. anthrasis* pXO1+/pXO2− lysates provided positive or equivocal results. Lysates made from a 2:1 mixture of *B. cereus* and *B. anthracis* pXO1+/pXO2+ provided equivocal results (31,925 mean RLU). The cumulative results of the tests performed on the experimental samples (i.e., not including the control samples) are presented in Table 2.

TABLE 2

Results Obtained with Different Species and Strains of Bacteria

| Genus species | Strains tested | Results Positive | Negative | Equivocal |
|---|---|---|---|---|
| *B. anthracis* | 25 | 24 | 0 | 1 (pX01 + /pX02-strain) |
| *B. alvei* | 1 | 0 | 1 | 0 |
| *B. amyloliquefaciens* | 1 | 0 | 1 | 0 |
| *B. badius* | 1 | 0 | 1 | 0 |
| *B. cereus* | 5 | 0 | 5 | 0 |
| *B. circulans* | 1 | 0 | 1 | 0 |
| *B. coagulans* | 1 | 0 | 1 | 0 |
| *B. epiphytus* | 1 | 0 | 1 | 0 |
| *B. firmus* | 1 | 0 | 1 | 0 |
| *B. lentus* | 1 | 0 | 1 | 0 |
| *B. licheniformis* | 1 | 0 | 1 | 0 |
| *B. megaterium* | 2 | 0 | 2 | 0 |
| *B. mycoides* | 1 | 0 | 1 | 0 |
| *B. pumilus* | 1 | 0 | 1 | 0 |
| *B. sphaericus* | 1 | 0 | 1 | 0 |
| *B. subtilis, globigii* | 1 | 0 | 1 | 0 |
| *B. thuringiensis* | 5 | 0 | 5 | 0 |
| *Bacillus* (unknown species) | 1 | 0 | 1 | 0 |
| *Brevibacillus laterosporus* | 1 | 0 | 1 | 0 |
| *Paenibacillus alevi* | 1 | 0 | 1 | 0 |
| *Paenibacillus macerans* | 1 | 0 | 1 | 0 |
| *Paenibacillus polymyxa* | 1 | 0 | 1 | 0 |
| *Brucella canis* | 3 | 0 | 3 | 0 |
| *Burholderia thailandiensis* | 1 | 0 | 1 | 0 |
| *Francisella philomiragia* | 1 | 0 | 1 | 0 |
| *Francisella tularensis* | 1 | 0 | 1 | 0 |
| *Ochrobacterium* (unknown species) | 5 | 0 | 5 | 0 |
| *Vibrio parahaemolyticus* | 1 | 0 | 1 | 0 |
| *Yersinia enterocoltica* | 1 | 0 | 1 | 0 |
| *Yersinia pestis* | 1 | 0 | 1 | 0 |

These tests included 61 separate assays performed on 24 samples known to contain *B. anthracis* (pXO1+/pXO2+) strains and 130 assays performed on samples that included 16 other *Bacillus* species and 28 non-anthrax species (including *Yersinia, Brucella, Burkholderia, Vibrio, Brevibacillus*, and *Paenibacillus*), and at least 39 different strains. For *B. anthracis*-containing samples, the results had a mean of 62,400 RLU, a median of 64,900 RLU, and the sensitivity of the assay was 98.4%. For the samples that did not contain *B. anthracis*, the results had a mean of 4,520 RLU, a median of 4,000 RLU, and the specificity of the assay was 98.5%. These results show that the assay effectively detects *B. anthracis* present in lysates made from biological samples.

EXAMPLE 4

Detection of 23S rRNA Sequences in a *B. cereus* Complex Group Species

This example shows that 23S rRNA sequences and DNA encoding rRNA can be detected for members of the *B. cereus* complex group by using an oligonucleotide probe of SEQ ID NO:35 specific for the target sequence of SEQ ID NO:32. This example also shows that hybridization of the probe and target sequences after 20 min incubation was sufficient to allow detection of the hybridization complexes. For these tests, the probe oligonucleotide of SEQ ID NO:35 was labeled with AE using a linker to the oligonucleotide between residues 10 and 11.

To show the specificity of the labeled probe for the *B. cereus* complex group organisms, *B. cereus* and *B. megaterium* cells were grown overnight on blood agar plates and three 1-μl loopfuls of cells for each organism were collected for each test sample. The cells were suspended in 0.15 ml of lysis reagent (0.1% LLS, 20 mM lithium succinate, pH 5.5, 1 mM EDTA), vortex mixed for 10 sec, and the mixture was heated at 100° C. for 15 min to lyse the cells, and the lysate was vortexed for 5 sec. For one set of controls, 5 μl of each lysate was diluted into 1 ml of a solution (0.4 M LiOH, 0.4 M HCl, 50 mM lithium succinate), from which 0.1 ml was taken for hybridization testing using a positive control labeled probe (SEQ ID NO:40), with unlabeled helper oligomers (SEQ ID NO:41, SEQ ID NO:42 and SEQ ID NO:43) that bind to eubacterial sequences of rRNA and DNA encoding rRNA (Hogan et al., U.S. Pat. No. 5,679,520), i.e., sequences in both *B. cereus* and *B. megaterium*. The remaining portion of lysate was processed under basic conditions (referred to as "base-processed") by mixing it with 0.1 ml of 2 M LiOH (final concentration, 0.8 M LiOH) and heating at 60° C. for 15 min, and then 0.25 ml of a neutralizing reagent (0.8 M HCl, 100 mM Li-succinate) was added which resulted in a pH of between 5 to 5.5. A lysate contains both DNA and RNA, whereas a base-processed lysate is expected to contain DNA but little or no RNA.

For the hybridization reactions (performed in duplicate for each sample), 0.1 ml of the lysate (diluted 1:300) or base-processed lysate was mixed independently with each of the tested AE-labeled oligonucleotide probes (about 0.2 pmol) to provide about $2\times10^7$ RLU per reaction. Each mixture was incubated at 60° C. for 45 min to allow hybridization, and then 0.3 ml of selection reagent (182 mM NaOH, 600 mM boric acid, 1% v/v TRITON® X-100) was added and the mixture was incubated at 60° C. for 10 min to hydrolyze the label on unbound labeled probes in the homogenous reaction mixture. The luminescent signal (RLU) from bound probes was then detected for 2 sec in a luminometer (LEADER® 450, Gen-Probe Incorporated, San Diego, Calif.). A negative control was treated identically but contained only probe and no bacterial target nucleic acid ("none").

Results of these tests are shown in Table 3, showing the average (mean) RLU of duplicate hybridization reactions detected for each sample. For the lysates that were not base-processed (column 5), the hybridization signals detected by using the labeled probe of SEQ ID NO:40 (with helper oligomers) detect hybridization to both rRNA and DNA encoding rRNA (rDNA) because the RNA was not hydrolyzed during sample preparation. The results for the base-processed samples (columns 3 and 4) detect hybridization to rDNA because in those samples RNA was hydrolyzed.

TABLE 3

Detection of rRNA and rDNA in *B. cereus* Compared to *B. megaterium*

| Species | Sample | Labeled Probe SEQ ID NO:35 base-processed | SEQ ID NO:40 base-processed | SEQ ID NO:40 lysate |
|---|---|---|---|---|
| *B. cereus* | 1 | 207,927 | 108,172 | 1,603,371 |
| | 2 | 77,923 | 55,187 | 1,271,894 |
| | 3 | 82,375 | 54,152 | 650,58;6 |

TABLE 3-continued Detection of rRNA and rDNA in *B. cereus* Compared to *B. megaterium*

| | | Labeled Probe | | |
| --- | --- | --- | --- | --- |
| Species | Sample | SEQ ID NO:35 base-processed | SEQ ID NO:40 base-processed | SEQ ID NO:40 lysate |
| *B. megaterium* | 1 | 970 | 27,268 | 78,726 |
| | 2 | 856 | 13,665 | 127,474 |
| | 3 | 777 | 11,332 | 99,668 |
| None | | 485 | 1,557 | |

These results show that the SEQ ID NO:35 probe (column 3) provided a positive signal for the *B. cereus* samples and a significantly diminished signal, i.e. negative results, for the samples that contained *B. megaterium*, a *Bacillus* species that is not in the *B. cereus* complex group. Thus, SEQ ID NO:35 is a probe that distinguishably recognizes a *B. cereus* complex species from other *Bacillus* species. The labeled SEQ ID NO:40 probe (columns 4 and 5) for the eubacterial target sequence provided a positive signal (greater than 10,000 RLU) for all of the samples and serves as an internal positive control for the assay which shows that the sample processing and hybridization steps were appropriately performed and that the samples contained sufficient numbers of the target nucleic acids to produce a positive signal.

In similar experiments, the hybridization incubation times were shortened in assays using the labeled probe of SEQ ID NO:35 and samples containing *B. cereus*. Using the procedures described above, samples of *B. cereus* (two 1-μl loopfuls from overnight growth on blood agar) were collected and lysed, base-processed, and hybridized with the labeled probe for between 20 and 45 min. For samples 1 and 2, lysis was 10 min, base-processing was 10 min, and hybridization was 40 min; and for samples 3 to 8, lysis was 15 min, base-processing was 15 min, and hybridization was 20 to 45 min. as shown in Table 4. Then, for all samples, the hybridization mixtures were treated with selection reagent and signals (RLU) were detected as described above. The positive control was a mixture of lysis and hybridization reagents at the same final concentrations as in the experimental samples, but a synthetic DNA oligomer (SEQ ID NO:32) was added instead of the lysate. The negative control was a similar mixture of reagents to which only the labeled probe oligomer was added (i.e., no target nucleic acid). The results of these assays (mean RLU of duplicate tests) are shown in Table 4.

TABLE 4

Detection of 23S rRNA with SEQ ID NO:35 After Varying Hybridization Times

| Sample | Lysis/Base-process | Hybridize | Detected Signal (RLU) |
| --- | --- | --- | --- |
| 1 | 10 min/10 min | 40 min | 68,408 |
| 2 | | | 81,354 |
| 3 | 15 min/15 min | 20 min | 102,889 |
| 4 | | | 78,218 |
| 5 | 15 min/15 min | 30 min | 79,828 |
| 6 | | | 114,837 |
| 7 | 15 min/15 min | 45 min | 91,222 |
| 8 | | | 71,015 |
| Negative control | not applicable | 45 min | 437 |
| Positive control | not applicable | 45 min | 233,362 |

These results show that the probe of SEQ ID NO:35 detects the presence of *B. cereus* complex group rRNA in a sample using a variety of conditions and as little as 20 min of hybridization.

EXAMPLE 5

Detection of capB Target Sequences

In these experiments, probes specific for capB target sequences were tested using a capB sequence (SEQ ID NO:34) cloned into a plasmid as the target nucleic acid. The plasmid DNA containing SEQ ID NO:34 was isolated from transfected *E. coli* cells by using standard methods, quantitated by using standard spectrometry procedures, and used in the hybridization tests as either intact circular plasmid or linear plasmid DNA (i.e., linearized by cutting with a restriction endonuclease). The target DNA was assayed at $2 \times 10^7$ to $2 \times 10^9$ copies per hybridization reaction ($2 \times 10^7$ and $2 \times 10^8$ for circular DNA, and $2 \times 10^8$ and $2 \times 10^9$ for linear DNA). The labeled probes were oligomers of SEQ ID NO: 9 or SEQ ID NO:11, which were used in the hybridization reactions with or without additional unlabeled oligonucleotides (SEQ ID NO:10, SEQ ID NO:11, SEQ ID NO:12). The unlabeled oligonucleotides had previously been AE-labeled via linker arms, but the AE labels had been hydrolyzed before the oligonucleotides were used in these reactions.

The reactions were prepared as mock lysates using substantially the same procedures as describe in Example 4. Briefly, plasmid DNA (10 μl containing about $10^8$, $10^9$ or $10^{10}$ copies) was mixed with lysis reagent, with or without unlabeled oligonucleotides (10 pmol each of SEQ ID:10 and SEQ ID NO:11 or SEQ ID:10 and SEQ ID NO:12, as shown in Table 5) in a final volume of 150 μl, and heated at 100° C. for 15 min to mimic lysis conditions. Then, 100 μl of 2 M LiOH was added and mixed, and the mixture was heated at 60° C. for 15 min. Then, 250 μl of a neutralizing reagent (0.8 M HCl, 100 mM Li-succinate) was added to result in pH 5 to 5.5. Before hybridization, the target-containing mixtures were either heated at 100° C. for 5 min and then rapidly cooled on ice (100° C. prehybridization), or were allowed to remain at room temperature (RT prehybridization). Duplicate aliquots of 100 μl of each mixture were tested for hybridization with AE-labeled probes of SEQ ID NO:9 or SEQ ID NO:11 equivalent to about $2 \times 10^7$ RLU per reaction (i.e., about 0.2 pmol) by adding the probes and incubating the mixture at 60° C. for 45 min. Then, to inactivate the label on unbound probes, 300 μl of selection reagent was added to each reaction mixture followed by incubation at 60° C. for 10 min, and the luminescence (RLU) was detected by using a luminometer as previously described. For these tests, negative controls for the labeled probes were similar composition mixtures that contained labeled probe oligomers but no target DNA or unlabeled oligomers, and negative controls for the unlabeled oligomers were similar composition mixtures that contained the unlabeled oligomers and target DNA ($2 \times 10^8$ to $2 \times 10^9$ copies/reaction) but no labeled probe oligomers. All controls were treated as for the experimental test samples. The results (mean RLU detected) of these assays are shown in Table 5.

TABLE 5

Detection of capB Target Sequences

| Labeled Probe | Target (Form, Copies, Prehybridization Temp.) | Unlabeled Oligomers | Detected Signal (mean RLU) |
| --- | --- | --- | --- |
| SEQ ID NO:9 | circular, $2 \times 10^7$, RT | SEQ ID NOs:10 & 11 | 3,014 |
| | | None | 3,276 |
| | circular, $2 \times 10^7$, 100° C. | SEQ ID NOs:10 & 11 | 4,998 |
| | | None | 3,033 |

TABLE 5-continued

Detection of capB Target Sequences

| Labeled Probe | Target (Form, Copies, Prehybridization Temp.) | Unlabeled Oligomers | Detected Signal (mean RLU) |
|---|---|---|---|
| SEQ ID NO:9 | circular, $2 \times 10^8$, RT | SEQ ID NOs:10 & 11 | 20,338 |
| | | None | 18,644 |
| | circular, $2 \times 10^8$, 100° C. | SEQ ID NOs:10 & 11 | 18,329 |
| | | None | 13,190 |
| SEQ ID NO:9 | linear, $2 \times 10^8$, RT | SEQ ID NOs:10 & 11 | 13,317 |
| | | None | 13,526 |
| | linear, $2 \times 10^8$, 100° C. | SEQ ID NOs:10 & 11 | 14,095 |
| | | None | 13,351 |
| SEQ ID NO:9 | linear, $2 \times 10^9$, RT | SEQ ID NOs:10 & 11 | 99,961 |
| | | None | 94,097 |
| | linear, $2 \times 10^9$, 100° C. | SEQ ID NOs:10 & 11 | 95,507 |
| | | None | 90,963 |
| SEQ ID NO:11 | circular, $2 \times 10^7$, RT | SEQ ID NOs:10 & 12 | 2,899 |
| | | None | 2,590 |
| | circular, $2 \times 10^7$, 100° C. | SEQ ID NOs:10 & 12 | 2,184 |
| | | None | 2,105 |
| SEQ ID NO:11 | circular, $2 \times 10^8$, RT | SEQ ID NOs:10 & 12 | 15,764 |
| | | None | 14,844 |
| | circular, $2 \times 10^8$, 100° C. | SEQ ID NOs:10 & 12 | 15,286 |
| | | None | 15,124 |
| SEQ ID NO:11 | linear, $2 \times 10^8$, RT | SEQ ID NOs:10 & 12 | 11,816 |
| | | None | 11,579 |
| | linear, $2 \times 10^8$, 100° C. | SEQ ID NOs:10 & 12 | 11,353 |
| | | None | 11,809 |
| SEQ ID NO:11 | linear, $2 \times 10^9$, RT | SEQ ID NOs:10 & 12 | 81,044 |
| | | None | 72,891 |
| | linear, $2 \times 10^9$, 100° C. | SEQ ID NOs:10 & 12 | 83,307 |
| | | None | 76,653 |
| None (Control) | circular, $2 \times 10^8$ | SEQ ID NOs:10 & 11 | 102 |
| None (Control) | linear, $2 \times 10^9$ | SEQ ID NOs:10 & 11 | 224 |
| None (Control) | circular, $2 \times 10^8$ | SEQ ID NOs:10 & 12 | 105 |
| None (Control) | linear, $2 \times 19^9$ | SEQ ID NOs:10 & 12 | 276 |
| SEQ ID NO:9 | None (Control) | None (Control) | 558 |
| SEQ ID NO:11 | None (Control) | None (Control) | 1,113 |

The results illustrate that probes of both SEQ ID NO:9 and SEQ ID NO:11 effectively hybridized to and detected the capB target sequence at all copy numbers tested ($2 \times 10^7$ to $2 \times 10^9$ copies per reaction). Both probes detected the capB target sequence in either circular or linear DNA. Prehybridization heating of the target-containing sample to 100° C. compared to room temperature (RT) samples did not significantly affect detection of the capB target, and in many cases greater RLU were detected for the RT sample compared to the corresponding heated sample. A detectable signal greater than background (RLU of controls for labeled probes) was obtained for all experimental samples even without use of unlabeled oligonucleotides. These results show that a variety of sample conditions may be used to effectively detect the capB target sequence by hybridization with the probes of SEQ ID NO:9 and SEQ ID NO:11.

In a similar set of assays, a combination of probes of SEQ ID NO:9 and SEQ ID NO: 11 were used in an assay with or without unlabeled oligomers of SEQ ID NO:10 and SEQ ID NO:12. The target capB sequence (SEQ ID NO:34) was included in the experimental samples as circular plasmid DNA, as described above, using $2 \times 10^8$ and $2 \times 10^9$ copies per hybridization reaction. Essentially the same procedures as described above were performed except that both labeled probes, SEQ ID NO:9 and SEQ ID NO:11, were added to the same hybridization reaction mixture, each equivalent to about $2 \times 10^7$ RLU and about 0.2 pmol per reaction. The results of these tests are shown in Table 6 (mean RLU of duplicate samples).

TABLE 6

Detection of capB Target Sequences with Combined Probes

| Labeled Probes | Target (Copies/reaction, Prehyb. Temp.) | Unlabeled Oligomers | Detected Signal (mean RLU) |
|---|---|---|---|
| SEQ ID NOs:9 & 11 | $2 \times 10^8$, RT | SEQ ID NOs:10 & 12 | 33,016 |
| | | None | 34,196 |
| | $2 \times 10^8$, 100° C. | SEQ ID NOs:10 & 12 | 32,912 |
| | | None | 30,570 |
| SEQ ID NOs:9 & 11 | $2 \times 10^9$, RT | SEQ ID NOs:10 & 12 | 231,475 |
| | | None | 210,236 |
| | $2 \times 10^9$, 100° C. | SEQ ID NOs:10 & 12 | 215,339 |
| | | None | 193,816 |
| SEQ ID NOs:9 & 11 | None (Control) | None (Control) | 808 |

The results illustrate that hybridization by using multiple labeled probes that bind specifically to different capB target sequences provided a higher detected signal that was approximately additive of the signals obtained using each probe independently (i.e., compare the results of Table 6 with those of Table 5 for each probe hybridized alone for the same number of circular target). These results also show that increased positive signals were obtained in some cases when unlabeled oligomers were included in the reaction mixtures although the unlabeled oligomers were not necessary to obtain positive signals.

Similar procedures were used to demonstrate detection of both the capB and the pagA targets individually and in the same assay as described in the next example.

EXAMPLE 6

Detection of capB and pagA Sequences by Hybridization

This example detected plasmid-borne capB and pagA sequences in samples prepared using methods similar to those described in Example 5 by using labeled capB-specific probes of SEQ ID NO:9 and SEQ ID NO:11, and labeled pagA-specific probes of SEQ ID NO:4 and SEQ ID NO:7, with or without unlabeled oligomers that could act as helpers. The capB-specific unlabeled oligomers were of SEQ ID NO:10 and SEQ ID NO:12, and the pagA-specific unlabeled oligomers were of SEQ ID NO:3 and SEQ ID NO:8. Circular plasmid DNAs containing the capB and pagA target sequences (SEQ ID NO:34 and SEQ ID NO:33, respectively, as described in Example 1) were used at $2 \times 10^8$ and $2 \times 10^9$ copies per hybridization reaction.

Briefly, plasmid DNA (10 μl containing about $10^9$ or $10^{10}$ copies) was mixed with lysis reagent, with or without unlabeled oligonucleotides (10 pmol of each) in a final volume of 150 μl, and heated at 100° C. for 15 min. Then, 100 μl of 2 M LiOH was added, mixed, and the mixture was heated at 60° C. for 15 min. Then, 250 μl of a neutralizing reagent (0.8 M HCl, 100 mM Li-succinate) was added to result in pH 5 to 5.5 of the mixture at RT. Four 100-μl aliquots of each mixture were hybridized with the combinations of AE-labeled probes as shown in Table 7, using about 0.2 pmol, equivalent to about $2 \times 10^7$ RLU, for each probe per reaction and the mixtures were incubated at 60° C. for 45 min. Then, 300 μl of selection reagent was added to each mixture which was incubated at 60° C. for 10 min to inactivate the label on unbound probes, and the luminescence (RLU) was detected for the bound labeled probes. Negative controls included probes alone in similar composition mixtures, and unlabeled oligomers with target DNA in similar composition mixtures, all of which were treated as for the test samples. The results (mean RLU detected for four test samples, or duplicates for the controls) of these assays are shown in Table 7.

TABLE 7

Detection of capB and pagA Target Sequences in Plasmid DNA

| Labeled Probes | Target, Copies | Unlabeled Oligomers | Mean RLU |
|---|---|---|---|
| SEQ ID NOs:9 & 11 | capB, $2 \times 10^8$ | SEQ ID NOs:10 & 12 | 30,920 |
| | | None | 29,731 |
| | capB, $2 \times 10^9$ | SEQ ID NOs:10 & 12 | 210,066 |
| | | None | 192,718 |
| SEQ ID NOs:4 & 7 | pagA, $2 \times 10^8$ | SEQ ID NOs:3 & 8 | 18,375 |
| | | None | 18,965 |
| | pagA, $2 \times 10^9$ | SEQ ID NOs:3 & 8 | 127,674 |
| | | None | 112,916 |
| SEQ ID NOs:4, 7, 9 & 11 | pagA & capB, $2 \times 10^8$ each | SEQ ID NOs:3, 8, 10 & 12 | 48,572 |
| | | None | 47,487 |
| | pagA & capB, $2 \times 10^9$ each | SEQ ID NOs:3, 8, 10 & 12 | 324,051 |
| | | None | 304,906 |
| SEQ ID NOs:9 & 11 | None (Control) | None | 405 |
| SEQ ID NOs:4 & 7 | None (Control) | None | 526 |
| SEQ ID NOs:4, 7, 9 & 11 | None (Control) | None | 1,057 |
| None (Control) | pagA, $2 \times 10^8$ & capB, $2 \times 10^9$ | SEQ ID NOs:3, 8, 10 & 12 | 122 |

The results illustrate that the assay detects both of the pagA and capB target genes present in plasmid DNA, individually and together in the same sample. In these assays, labeled probes specific for two target sequences, one in each of the pagA and capB target genes hybridized efficiently whether the unlabeled oligomers were present or not in the reaction mixtures.

The next example similarly used combinations of probes specific for the pagA and capB genes, along with a eubacterial control probe to detect target sequences in B. anthracis.

EXAMPLE 7

Detection of capB and pagA Sequences by Hybridization in B. anthracis

In these tests, samples were processed substantially as described in Example 4. The cells used were either B. anthracis (Sterne strain) or *B. cereus*. Briefly, cells were grown overnight on blood agar plates and one 1-μl loopful of cells were collected for each test sample, suspended in 0.15 ml of lysis reagent, mixed, and heated at 100° C. for 15 min to lyse the cells. For testing with the labeled probe of SEQ ID NO:40 (with unlabeled helper oligomers of SEQ ID NOs: 41, 42 and 43) for detection of eubacterial sequences, 5 μl of lysate was diluted into a 1 ml solution as described in Example 4, from which 0.1 ml was taken for hybridization testing to rRNA and/or DNA encoding rRNA sequences present in both *B. cereus* and *B. anthracis*. For each organism, lysates were used in hybridization without base processing or treated to make a base-processed lysate as described in Example 4. Duplicate samples were prepared and tested for the *B. athracis* lysates. The hybridization reactions were performed substantially as described in Example 4, using 0.1 ml of the diluted lysate or base-processed lysate mixed with AE-labeled probes (about 0.08 to 01 pmol each) to provide about 1×$10^7$ RLU per probe per reaction. The labeled probes were either a mixture of SEQ ID NO:4, SEQ ID NO:7, SEQ ID NO:9, and SEQ ID NO:11 to detect pagA and capB sequences as described in Example 6, or SEQ ID NO:40 (with unlabeled helper oligomers of SEQ ID NOS 41, 42 and 43) to detect rRNA or DNA encoding rRNA sequences common to eubacterial species (Hogan et al., U.S. Pat. No. 5,679,520). The hybridization reactions were incubated at 60° C. for 45 min, and then 0.3 ml of selection reagent was added and the mixtures were incubated at 60° C. for 10 min, after which luminescent signals (RLU) were detected in a luminometer (LEADER® 450). Negative controls contained no target nucleic acid but were composed of substantially the same reagents present in the experimental samples. Positive controls contained target nucleic acids that hybridize specifically to the respective probes, i.e., synthetic ssDNA containing the complementary pagA and capB sequences or *E. coli* rRNA containing a sequence complementary to the eubacterial probe. The results, shown in Table 8, are the mean RLU of four tests per sample for assays performed with probes of SEQ ID NOS 4, 7, 9 and 11, and mean RLU of two tests per sample for the negative controls and tests performed with the probe of SEQ ID NO:40 (with unlabeled oligomers of SEQ ID Nos. 41, 42 and 43).

Table 8

Probe Detection of Target Sequences in *B. anthracis* and *B. cereus*

| | SEQ ID NOS: | | |
|---|---|---|---|
| Sample & Preparation | 4, 7, 9 & 11 Base-processed | 4, 7, 9 & 11 Lysate | 40, 41, 42 & 43 Lysate |
| *B. anthracis* | 45,121 | 30,781 | 1,379,595 |
| *B. anthracis* | 42,271 | 29,941 | 1,099,156 |
| *B. cereus* | 1,803 | 3,329 | 761,356 |
| capB plasmid (Control) | 766,941 | not tested | not tested |
| pagA plasmid (Control) | 582,142 | not tested | not tested |
| *E. coil* rRNA (Control) | not tested | not tested | 44,834 |
| None (Control) | 739 | 772 | 262 |

As shown by these results, *B. anthracis* was detected by positive signals obtained by using the combination of probes (SEQ ID NOS 4, 7, 9, 11) specific for the pagA and capB target sequences and by using the probe specific for eubacterial rRNA (SEQ ID NO:40, with its helper oligomers). In contrast, *B. cereus* was negative in hybridization reactions using the probes specific for the pagA and capB target sequences but positive in hybridization reactions that used the probe for eubacterial rRNA sequences. Thus, the assay specific for the pagA and capB target sequences distinguishes *B. anthracis* from another species of the *B. cereus* complex group and the internal control probe (SEQ ID NO:40) for a eubacterial target sequence shows that the hybridization reactions were performed properly and had sufficient target present to be detected in all samples.

The invention is defined by the claims that follow which encompass the embodiments described and illustrated above.

We claim:

1. A composition comprising a synthetic oligonucleotide consisting of 25 to 40 nucleotides that hybridizes specifically to a B. anthracis pagA target sequence selected from the group consisting of SEQ ID Nos. 1, 2, 3, 4, 5, 6, 7, 8, 21, 22, 23, and 24, sequences fully complementary to SEQ ID Nos. 1, 2, 3, 4, 5, 6, 7, 8, 21, 22, 23, and 24, RNA equivalents of SEQ ID Nos. 1, 2, 3, 4, 5, 6, 7, 8, 21, 22, 23, and 24, and RNA sequences fully complementary to SEQ ID Nos. 1, 2, 3, 4, 5, 6, 7, 8, 21, 22, 23, and 24.

2. The composition of claim 1, wherein the synthetic oligonucleotide that hybridizes specifically to the pagA target sequence consists of SEQ ID NO:1 or SEQ ID NO:2.

3. The composition of claim 1, wherein the synthetic oligonucleotide that hybridizes specifically to the pagA target sequence consists of SEQ ID NO:3 or SEQ ID NO:4.

4. The composition of claim 1, wherein the synthetic oligonucleotide that hybridizes specifically to the pagA target sequence consists of SEQ ID NO:5 or SEQ ID NO:6.

5. The composition of claim 1, wherein the synthetic oligonucleotide that hybridizes specifically to the pagA target sequence consists of SEQ ID NO:7 or SEQ ID NO:8.

6. The composition of claim 1 further comprising a capB-specific synthetic oligonucleotide that hybridizes specifically to a capB target sequence, wherein the capB-specific oligonucleotide consists of SEQ ID NO:9, SEQ ID NO:10, SEQ ID NO:11, SEQ ID NO:12, SEQ ID NO:13 or SEQ ID NO:14.

7. The composition of claim 1, wherein the synthetic oligonucleotide has a DNA or RNA backbone, or mixed DNA and RNA backbone, or contains at least one 2'-methoxy RNA group linking the bases.

8. The composition of claim 1, wherein the synthetic oligonucleotide has a signal-producing label linked directly or indirectly to the oligonucleotide.

9. A kit comprising a synthetic oligonucleotide consisting of 25 to 40 nucleotides that hybridizes specifically to a sequence contained in a B. anthracis pagA target sequence selected from the group consisting of SEQ ID Nos. 1, 2, 3, 4, 5, 6, 7, 8, 21, 22, 23, and 24, sequences fully complementary to SEQ ID Nos. 1, 2, 3, 4, 5, 6, 7, 8, 21, 22, 23, and 24, RNA equivalents of SEQ ID Nos. 1, 2, 3, 4, 5, 6, 7, 8, 21, 22, 23, and 24, and RNA sequences fully complementary to SEQ ID Nos. 1, 2, 3, 4, 5, 6, 7, 8, 21, 22, 23, and 24.

10. The kit of claim 9, further comprising a capB-specific probe oligonucleotide consisting of SEQ ID NO: 9, 10, 11, 12, 13 or 14.

11. A method of detecting B. anthracis nucleic acid in a sample comprising the steps of:
   providing a sample containing B. anthracis nucleic acids;
   providing a pagA-specific probe that hybridizes specifically to a pagA target sequence, wherein the pagA-specific probe is a synthetic oligonucleotide of 25 to 40 nucleotides selected from the group consisting of SEQ ID Nos. 1, 2, 3, 4, 5, 6, 7, 8, 21, 22, 23, and 24, sequences fully complementary to SEQ ID Nos. 1, 2, 3, 4, 5, 6, 7, 8, 21, 22, 23, and 24, RNA equivalents of SEQ ID Nos. 1, 2, 3, 4, 5, 6, 7, 8, 21, 22, 23, and 24, and RNA sequences fully complementary to SEQ ID Nos. 1, 2, 3, 4, 5, 6, 7, 8, 21, 22, 23, and 24;
   hybridizing specifically at least one pagA-specific probe to the pagA target sequence; and
   detecting the presence of at least one pagA-specific probe hybridized to the pagA target sequence to indicate the presence of B. anthracis in the sample.

12. The method of claim 11 further comprising a capB-specific probe oligonucleotide consisting of SEQ ID NO:9, SEQ ID NO: 10, SEQ ID NO:11, SEQ ID NO:12, SEQ ID NO:13, or SEQ ID NO:14.

* * * * *

```
                            SEQUENCE LISTING

<160> NUMBER OF SEQ ID NOS: 43

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
cggtctggaa ccgtaggtcc agcac                                              25

<210> SEQ ID NO 2
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 2
cctctaatga atcagggatt ccatcattgt ca                                      32

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 3
cctgctagag atagtgaatg atcaattgcg                                         30

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 4
cccattgttt cagcccaagt tctttcc                                            27

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
acacgttgta gattggagcc gtccc                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
```

```
cctaacacta acgaagtcgt tggta                                          25

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 7
attaaccgcc gctatccgcc tttctacc                                       28

<210> SEQ ID NO 8
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 8
ccggtttagt cgtttctaat ggatcactag g                                   31

<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 9
ccaatatatc attcgcgcag atgtacc                                        27

<210> SEQ ID NO 10
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 10
cgcttaatcg gttgctcctc gtcagtaaa                                      29

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 11
gctcaccgat attaggacct tctttacgg                                      29

<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 12
cagcagcctc tttaactacc ctgcgtt                                        27

<210> SEQ ID NO 13
<211> LENGTH: 29
<212> TYPE: DNA
```

<213> ORGANISM: Artificial Sequence
<220> FEATURE:
<223> OTHER INFORMATION: Synthetic oligonucleotide

<400> SEQUENCE: 13
ggatgagcat tcaacatacc acggaatgc                              29

<210> SEQ ID NO 14
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 14
cgtgtaattc tcattgctcc tggatcc                                27

<210> SEQ ID NO 15
<211> LENGTH: 18
<212> TYPE: RNA
<213> ORGANISM: Artificial Sequence
<220> FEATURE:
<223> OTHER INFORMATION: Synthetic oligonucleotide

<400> SEQUENCE: 15
gccuuucaau uucgaacc                                          18

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
gcctttcaat ttcgaaccat gcg                                    23

<210> SEQ ID NO 17
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 17
atgcggttca aaatgttatc cggtattagc cccggtttcc                  40

<210> SEQ ID NO 18
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 18
gcgggtccat ccataagtga cagccgaagc c                           31

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19
gttcaaaatg ttatccggta ttagccccgg tttcc                       35

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 20
gcctttcaat ttcgaacc                                                 18

<210> SEQ ID NO 21
<211> LENGTH: 57
<212> TYPE: DNA
<213> ORGANISM: Bacillus anthracis

<400> SEQUENCE: 21
gtgctggacc tacggttcca gaccgtgaca atgatggaat ccctgattca ttagagg      57

<210> SEQ ID NO 22
<211> LENGTH: 57
<212> TYPE: DNA
<213> ORGANISM: Bacillus anthracis

<400> SEQUENCE: 22
cgcaattgat cattcactat ctctagcagg ggaaagaact tgggctgaaa caatggg      57

<210> SEQ ID NO 23
<211> LENGTH: 50
<212> TYPE: DNA
<213> ORGANISM: Bacillus anthracis

<400> SEQUENCE: 23
gggacggctc caatctacaa cgtgttacca acgacttcgt tagtgttagg              50

<210> SEQ ID NO 24
<211> LENGTH: 59
<212> TYPE: DNA
<213> ORGANISM: Bacillus anthracis

<400> SEQUENCE: 24
ggtagaaagg cggatagcgg cggttaatcc tagtgatcca ttagaaacga ctaaaccgg    59

<210> SEQ ID NO 25
<211> LENGTH: 112
<212> TYPE: DNA
<213> ORGANISM: Bacillus anthracis

<400> SEQUENCE: 25
ggtacatctg cgcgaatgat atattggttt actgacgagg agcaaccgat taagcgccgt   60
aaagaaggtc ctaatatcgg tgagcaacgc agggtagtta agaggctgc tg            112

<210> SEQ ID NO 26
<211> LENGTH: 56
<212> TYPE: DNA
<213> ORGANISM: Bacillus anthracis

<400> SEQUENCE: 26
gcattccgtg gtatgttgaa tgctcatccg gatccaggag caatgagaat tacacg       56

<210> SEQ ID NO 27
<211> LENGTH: 46
<212> TYPE: DNA

<213> ORGANISM: Artificial Sequence
<220> FEATURE:
<223> OTHER INFORMATION: Synthetic oligonucleotide

<400> SEQUENCE: 27
tttccaggtc gcttcgtcta cctcgttcct ttgtaactcc gtatag          46

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 28
ggttgttacc ctctacgacg gacc          24

<210> SEQ ID NO 29
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 29
gacctttcca ggtcgcttcg tctacctcgt tcctttgtaa ctccgtatag          50

<210> SEQ ID NO 30
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 30
gguuguuacc cucuacgacg          20

<210> SEQ ID NO 31
<211> LENGTH: 95
<212> TYPE: DNA
<213> ORGANISM: Artificial Sequence
<220> FEATURE:
<223> OTHER INFORMATION: Synthetic oligonucleotide for 16S rRNA sequence

<400> SEQUENCE: 31
ccgggaaacc ggggctaata ccggataaca ttttgaaccg catggttcga aattgaaagg          60
cggcttcggc tgtcacttat ggatggaccc gcgtc          95

<210> SEQ ID NO 32
<211> LENGTH: 80
<212> TYPE: DNA
<213> ORGANISM: Artificial Sequence
<220> FEATURE:
<223> OTHER INFORMATION: Synthetic oligonucleotide for 23S rRNA sequence

<400> SEQUENCE: 32
attctatacg gagttacaaa ggaacgaggt agacgaagcg acctggaaag gtccgtcgta          60
gagggtaaca accccgtagt          80

<210> SEQ ID NO 33
<211> LENGTH: 1108
<212> TYPE: DNA
<213> ORGANISM: Bacillus anthracis

<400> SEQUENCE: 33

-continued

```
gtacaagtgc tggacctacg gttccagacc gtgacaatga tggaatccct gattcattag      60
aggtagaagg atatacggtt gatgtcaaaa ataaagaac ttttctttca ccatggattt      120
ctaatattca tgaaagaaa ggattaacca aatataaatc atctcctgaa aaatggagca      180
cggcttctga tccgtacagt gatttcgaaa aggttacagg acggattgat aagaatgtat     240
caccagaggc aagacacccc cttgtggcag cttatccgat tgtacatgta gatatggaga     300
atattattct ctcaaaaaat gaggatcaat ccacacagaa tactgatagt gaaacgagaa     360
caataagtaa aaatacttct acaagtagga cacatactag tgaagtacat ggaaatgcag     420
aagtgcatgc gtcgttcttt gatattggtg ggagtgtatc tgcaggattt agtaattcga     480
attcaagtac ggtcgcaatt gatcattcac tatctctagc aggggaaaga acttgggctg     540
aaacaatggg tttaaatacc gctgatacag caagattaaa tgccaatatt agatatgtaa     600
atactgggac ggctccaatc tacaacgtgt taccaacgac ttcgttagtg ttaggaaaaa     660
atcaaacact cgcgacaatt aaagctaagg aaaaccaatt aagtcaaata cttgcaccta     720
ataattatta tccttctaaa aacttggcgc caatcgcatt aaatgcacaa gacgatttca     780
gttctactcc aattacaatg aattacaatc aatttcttga gttagaaaaa acgaaacaat     840
taagattaga tacggatcaa gtatatggga atatagcaac atacaatttt gaaaatggaa     900
gagtgagggt ggatacaggc tcgaactgga gtgaagtgtt accgcaaatt caagaaacaa     960
ctgcacgtat cattttaat ggaaaagatt taaatctggt agaaggcgg atagcggcgg     1020 ttaatcctag tgatccatta gaaacgacta accggatat gacattaaaa gaagcccta     1080 aaatagcatt tggatttaac gaaccgaa                                        1108
```

<210> SEQ ID NO 34
<211> LENGTH: 560
<212> TYPE: DNA
<213> ORGANISM: Bacillus anthracis

<400> SEQUENCE: 34

```
acaactggta catctgcgcg aatgatatat tggtttactg acgaggagca accgattaag      60
cgccgtaaag aaggtcctaa tatcggtgag caacgcaggg tagttaaaga ggctgctgat     120
ttagaagcag aagcacttat ttgtgaatgt atggcagttc aacccgatta tcaaattatc     180
ttccaaaata aaatgattca agcaaatgtt ggagtgattg taaatgtttt agaagatcat     240
atggatgtta tgggacctac acttgacgaa gtagctgaag cttcactgc taccattcca     300 tataatggac atttagtcac tattgaaagt gaatacttgg attactttaa agaggttgca     360
gaagagagaa atacaaaagt gattgttgcg gataattcta gaatttcaga agaattctta     420
cgaaaatttg attacatggt cttcccagat aatgcatcgc ttgctttagc ggtagcagag     480
gctcttggga ttgatgagga acagcattc cgtggtatgt tgaatgctca tccggatcca     540
ggagcaatga gaattacacg                                                  560
```

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35

```
gttaccctct acgacggacc                                                   20
```

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
ggtccgtcgt agagggtaac aacc                                         24

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37
cgcatggttc gaaattgaaa ggc                                          23

<210> SEQ ID NO 38
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 38
ggttcaaaat gttatccggt attagccccg gtttcc                            36

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
gcctttcaat ttcgaaccat gc                                           22

<210> SEQ ID NO 40
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 40
ggaacttacc cgacaaggaa tttcgctacc ttagg                             35

<210> SEQ ID NO 41
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 41
accgttatag ttacggccgc cgtttactgg ggcttc                            36

<210> SEQ ID NO 42
<211> LENGTH: 32
<212> TYPE: DNA
<213> ORGANISM: Artificial Sequence
<220> FEATURE:
<223> OTHER INFORMATION: Synthetic oligonucleotide

```
<400> SEQUENCE: 42
gcctggccat cgttacgcca ttcgtgcagg tc                                    32

<210> SEQ ID NO 43
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 43
gcccaaatcg ttacgccttt cgtgcgggtc                                       30
```